United States Patent
Alhadeff et al.

(10) Patent No.: US 12,350,448 B2
(45) Date of Patent: Jul. 8, 2025

(54) MODULAR MEDICAL DEVICES AND METHODS OF USING THE SAME

(71) Applicant: Boston Scientific Scimed Inc., Maple Grove, MN (US)

(72) Inventors: Daniel Davis Alhadeff, New York, NY (US); Aurora Bunten, Marco Island, FL (US); Evan Cusato, Long Beach, CA (US); Rachel Hwang, Campbell, CA (US); Harrison Young, Robbinsville, NJ (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 813 days.

(21) Appl. No.: 17/675,942

(22) Filed: Feb. 18, 2022

(65) Prior Publication Data

US 2022/0265967 A1 Aug. 25, 2022

Related U.S. Application Data

(60) Provisional application No. 63/151,336, filed on Feb. 19, 2021.

(51) Int. Cl.
  *A61M 25/01* (2006.01)
  *A61B 1/005* (2006.01)
  *A61B 1/012* (2006.01)

(52) U.S. Cl.
  CPC .... *A61M 25/0147* (2013.01); *A61M 25/0136* (2013.01); *A61B 1/0057* (2013.01); *A61B 1/012* (2013.01); *A61M 2025/015* (2013.01)

(58) Field of Classification Search
  CPC . A61B 1/00105; A61B 1/0052; A61B 1/0057; A61B 8/4411
  See application file for complete search history.

(56) References Cited

U.S. PATENT DOCUMENTS

| | | |
|---|---|---|
| 5,222,974 A | 6/1993 | Kensey et al. |
| 5,860,953 A | 1/1999 | Snoke et al. |
| 9,089,356 B2 | 7/2015 | Chen et al. |
| 9,107,573 B2 | 8/2015 | Birnkrant |
| 9,757,537 B2 | 9/2017 | Suon et al. |

(Continued)

FOREIGN PATENT DOCUMENTS

| | | |
|---|---|---|
| KR | 10-2011-0060785 A | 6/2011 |
| KR | 102161974 B1 | 10/2020 |

(Continued)

OTHER PUBLICATIONS

International Search Report issued on May 27, 2022, in International Patent Application No. PCT/US2022/017070 (42 pages, in English).

*Primary Examiner* — Deanna K Hall
(74) *Attorney, Agent, or Firm* — Bookoff McAndrews PLLC

(57) ABSTRACT

A medical device that includes a first body including a first actuation wire having a first connector that extends outwardly from the first body, and a second body including a second actuation wire having a second connector that is disposed within the second body. The first connector is configured to engage the second connector in response to the second body mating with the first body, and to deform the second connector in response to the first body disengaging the second body.

19 Claims, 21 Drawing Sheets

(56) References Cited

U.S. PATENT DOCUMENTS

| | | |
|---|---|---|
| 2008/0214896 A1 | 9/2008 | Krupa et al. |
| 2014/0275763 A1 | 9/2014 | King et al. |
| 2017/0188795 A1* | 7/2017 | Ouyang ................ A61B 1/015 |
| 2017/0245848 A1* | 8/2017 | Berkelaar ........ A61B 17/00234 |
| 2019/0313881 A1 | 10/2019 | Francher |
| 2020/0046209 A1 | 2/2020 | Francher |
| 2021/0068619 A1 | 3/2021 | Shin et al. |
| 2021/0068621 A1 | 3/2021 | Shin et al. |
| 2021/0068624 A1 | 3/2021 | Shin et al. |
| 2021/0068625 A1 | 3/2021 | Shin et al. |
| 2021/0068626 A1 | 3/2021 | Shin et al. |
| 2022/0151463 A1 | 5/2022 | Francher et al. |

FOREIGN PATENT DOCUMENTS

| | | |
|---|---|---|
| WO | WO 2022/109488 A1 | 5/2022 |
| WO | WO 2022/125550 A1 | 6/2022 |

\* cited by examiner

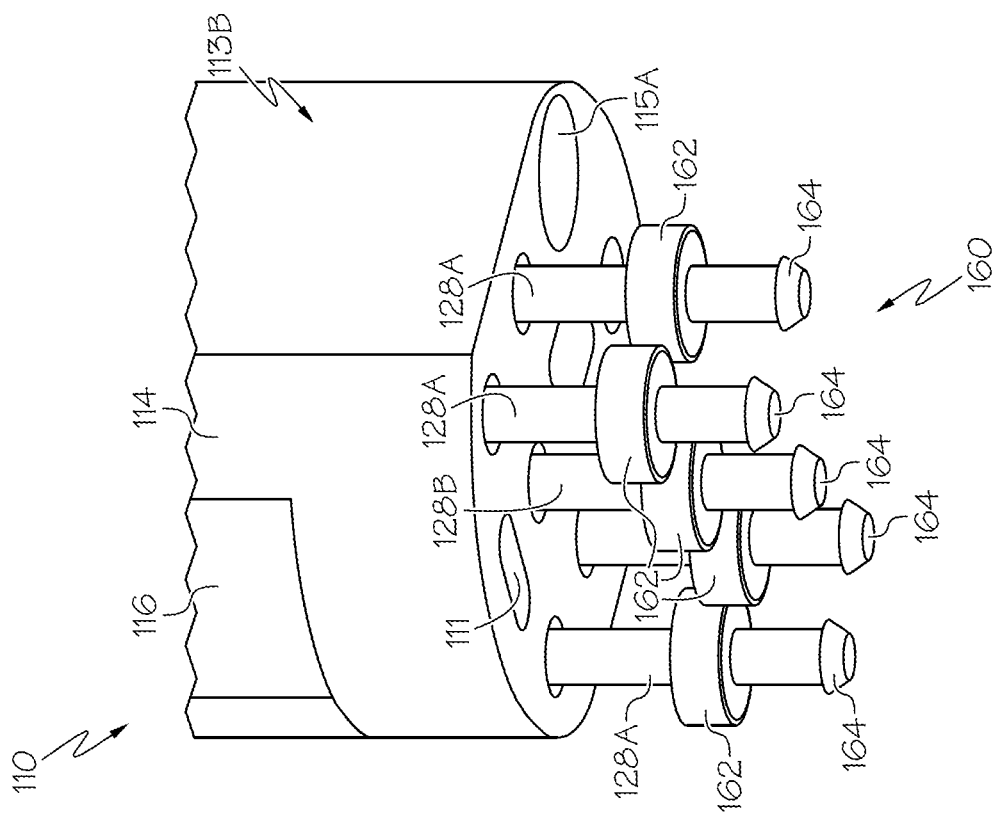
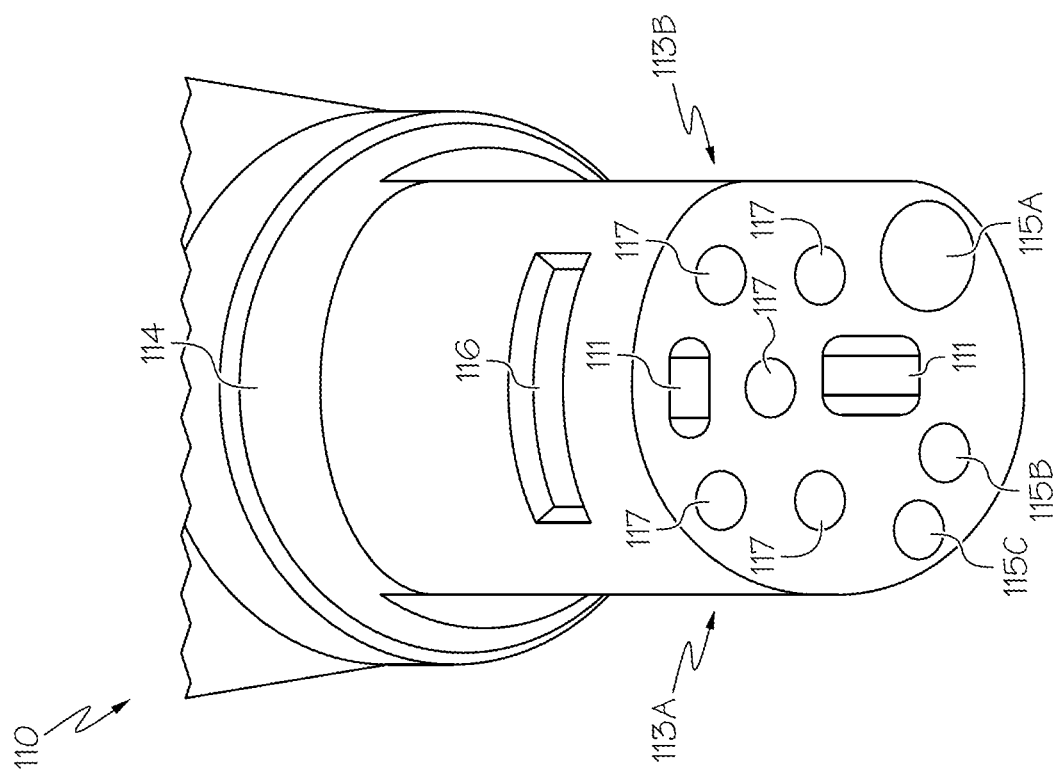
FIG. 6
FIG. 5

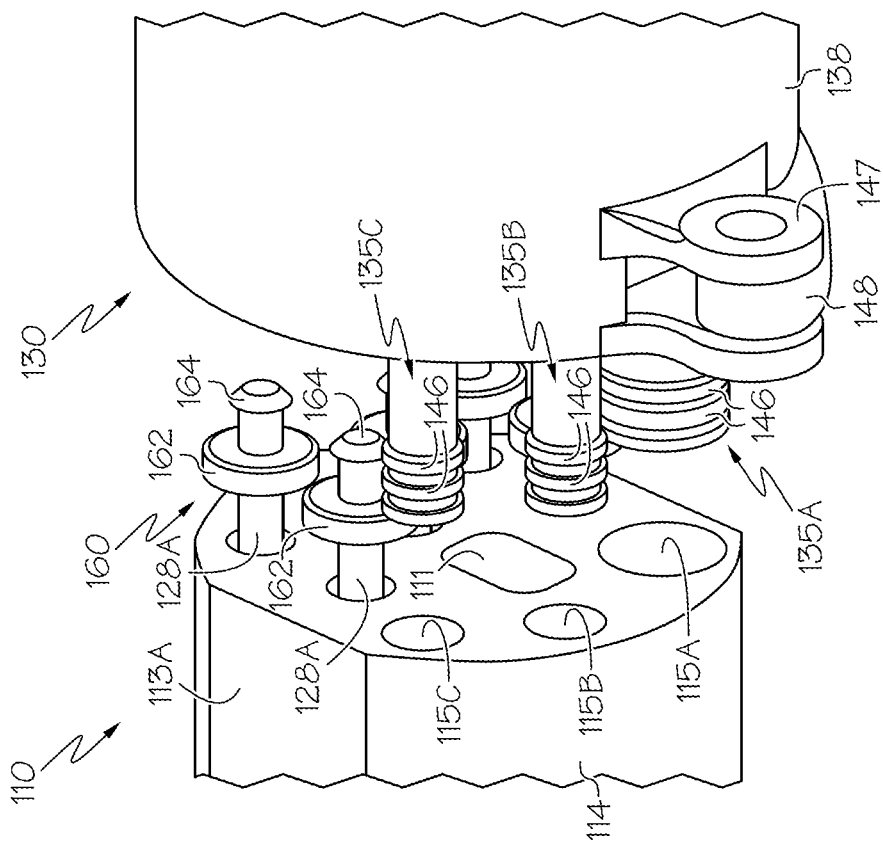
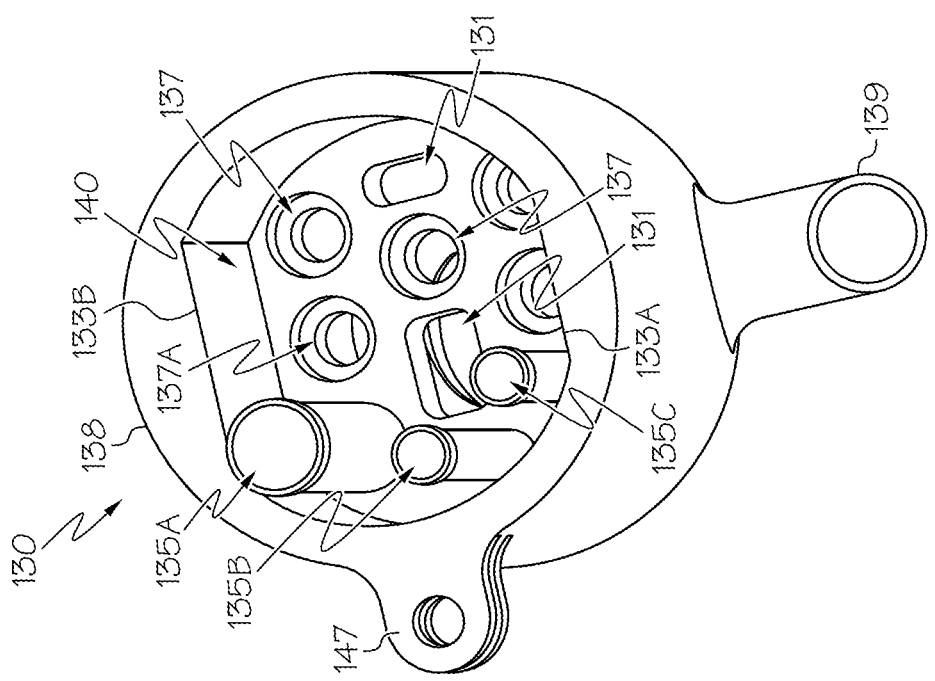
FIG. 8
FIG. 7

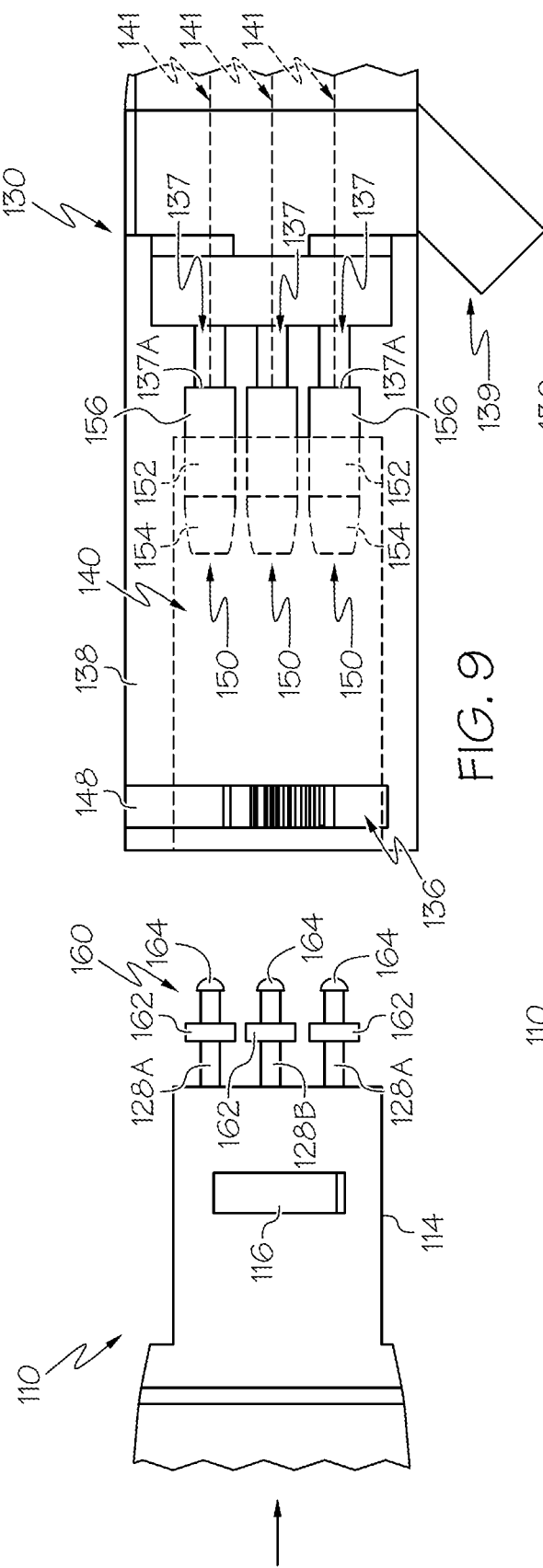
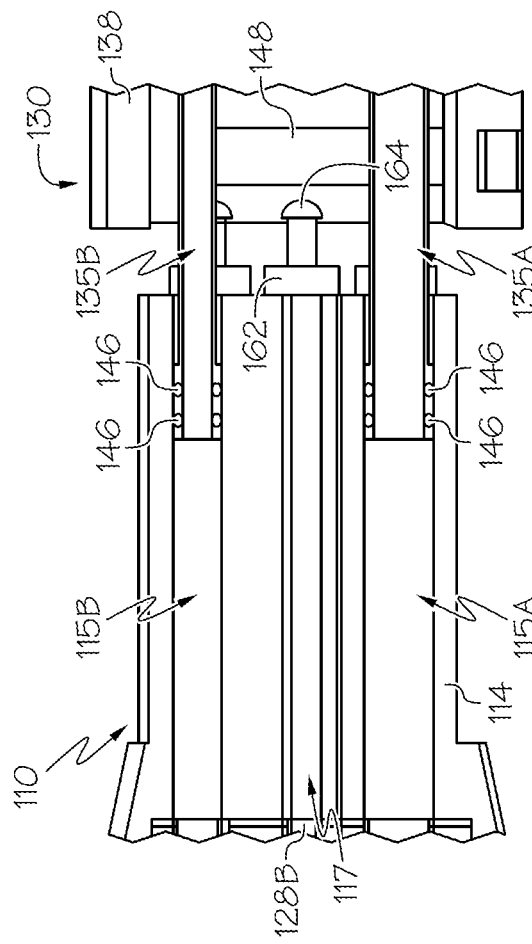
FIG. 9
FIG. 10

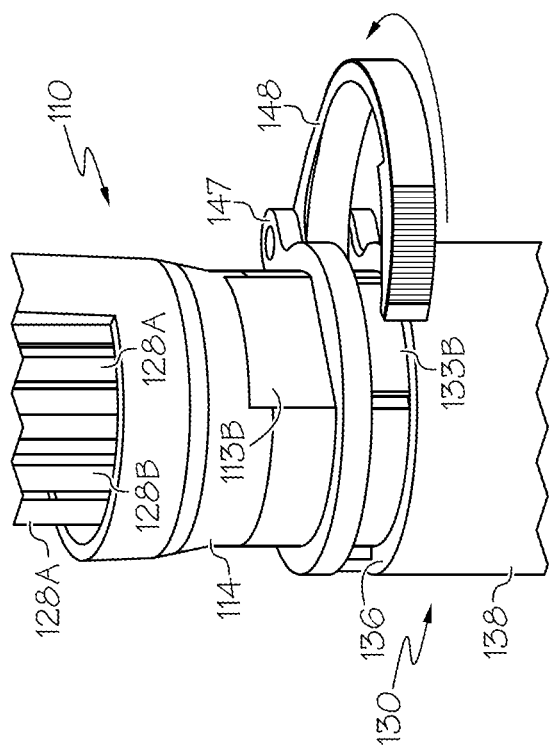
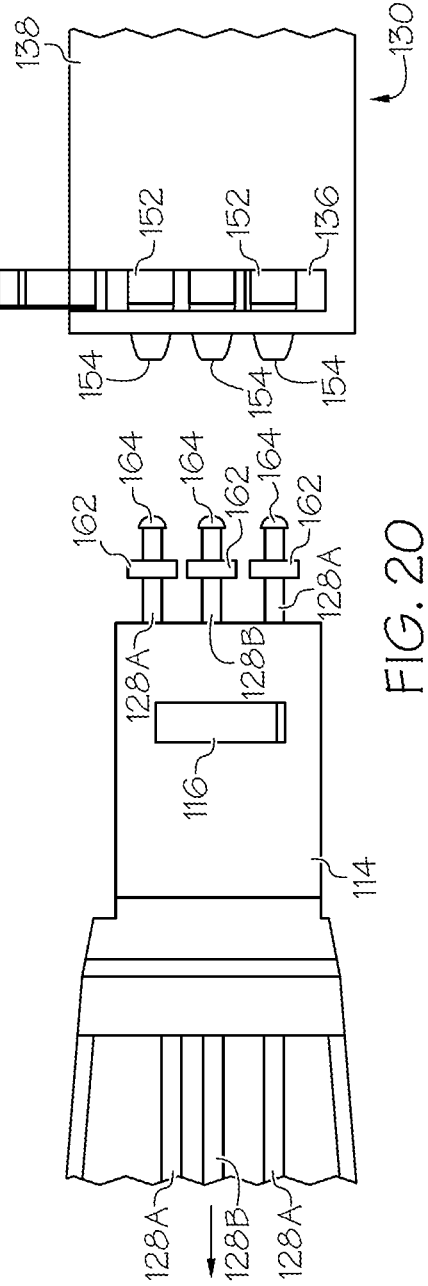

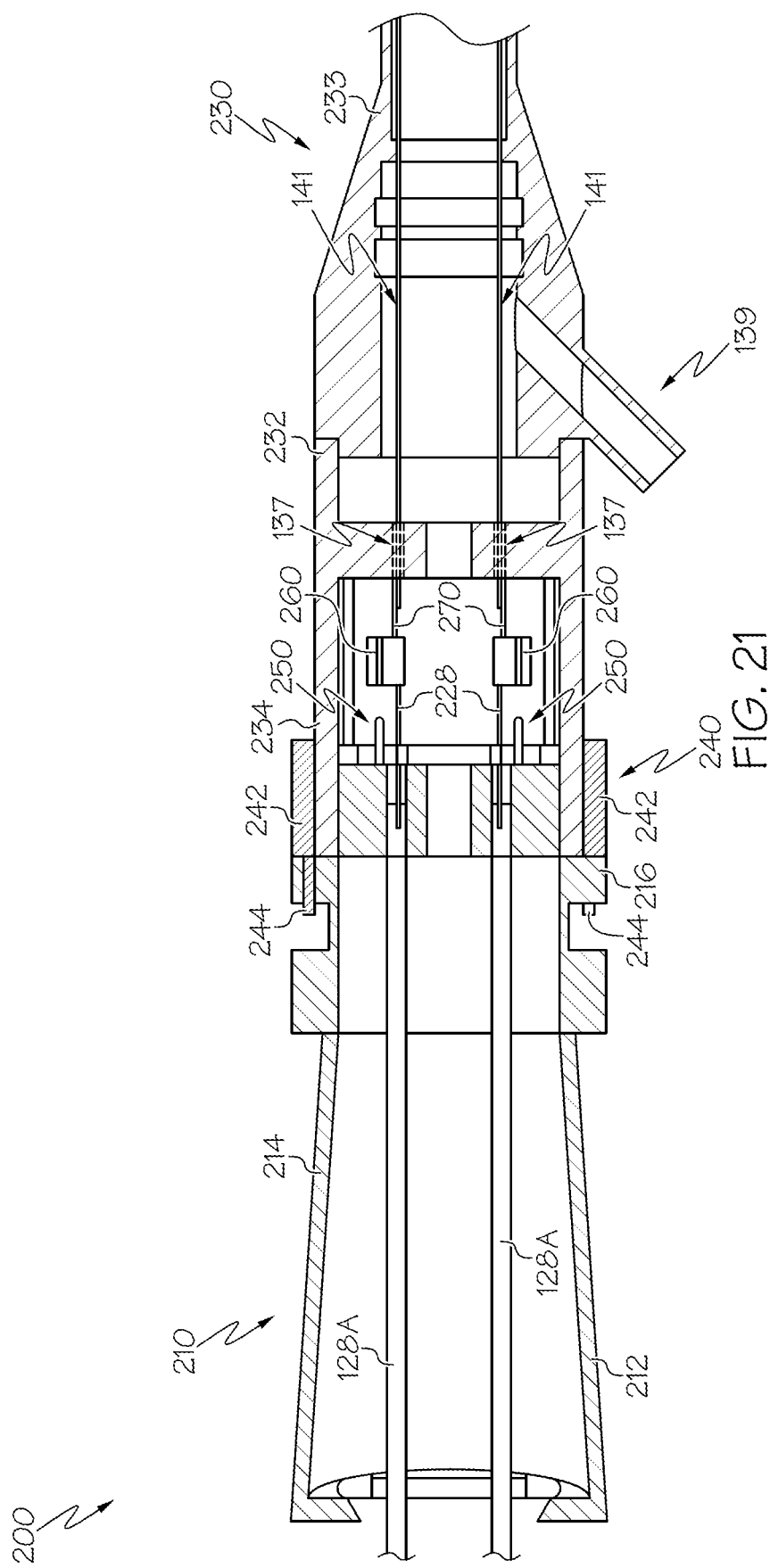

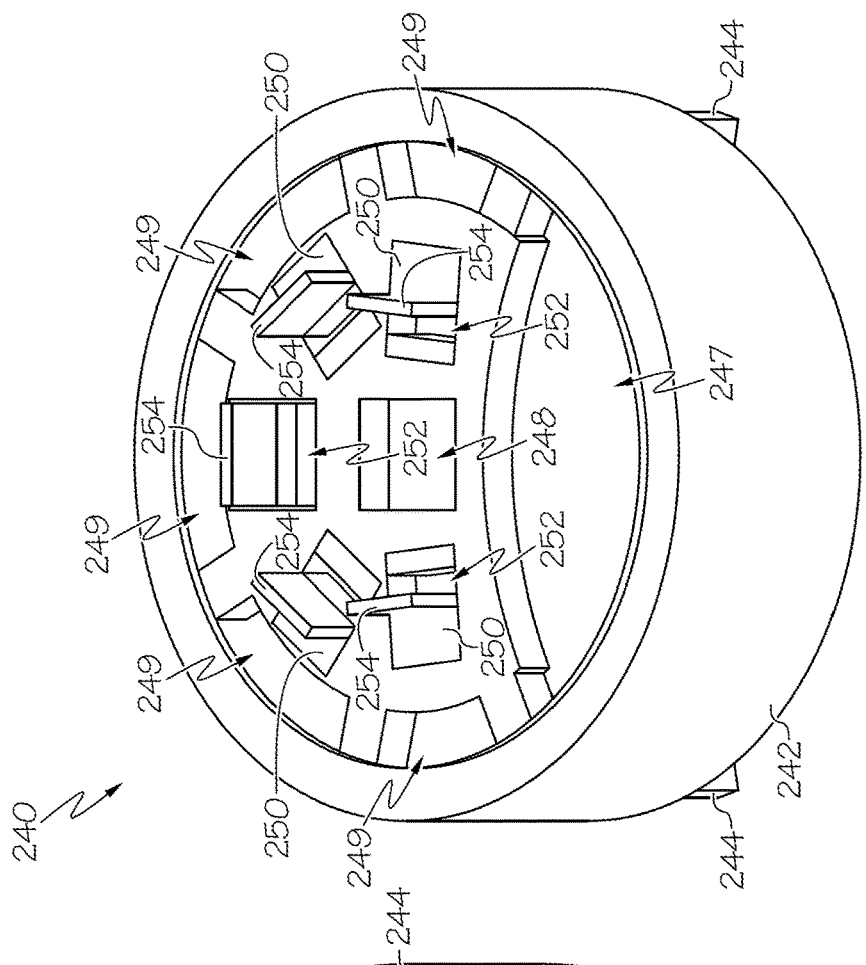
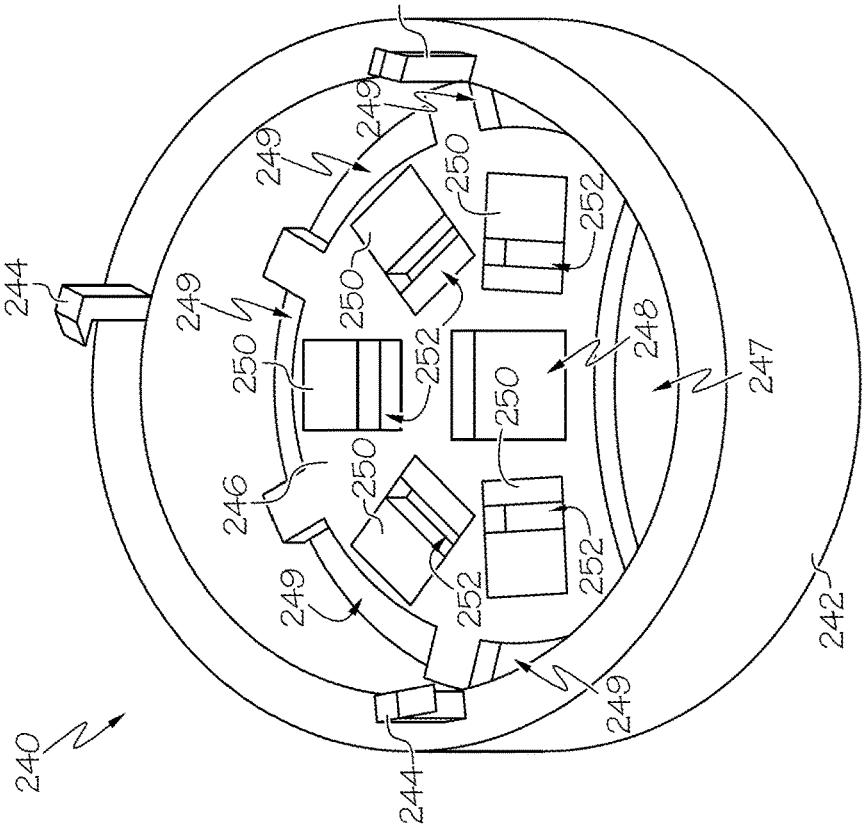

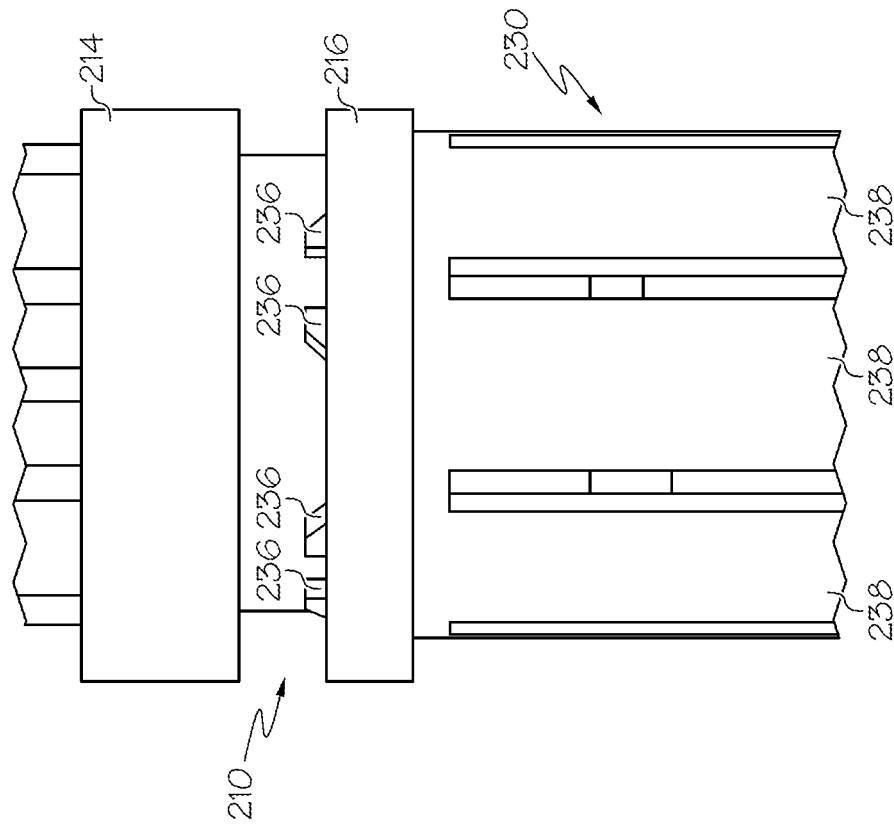
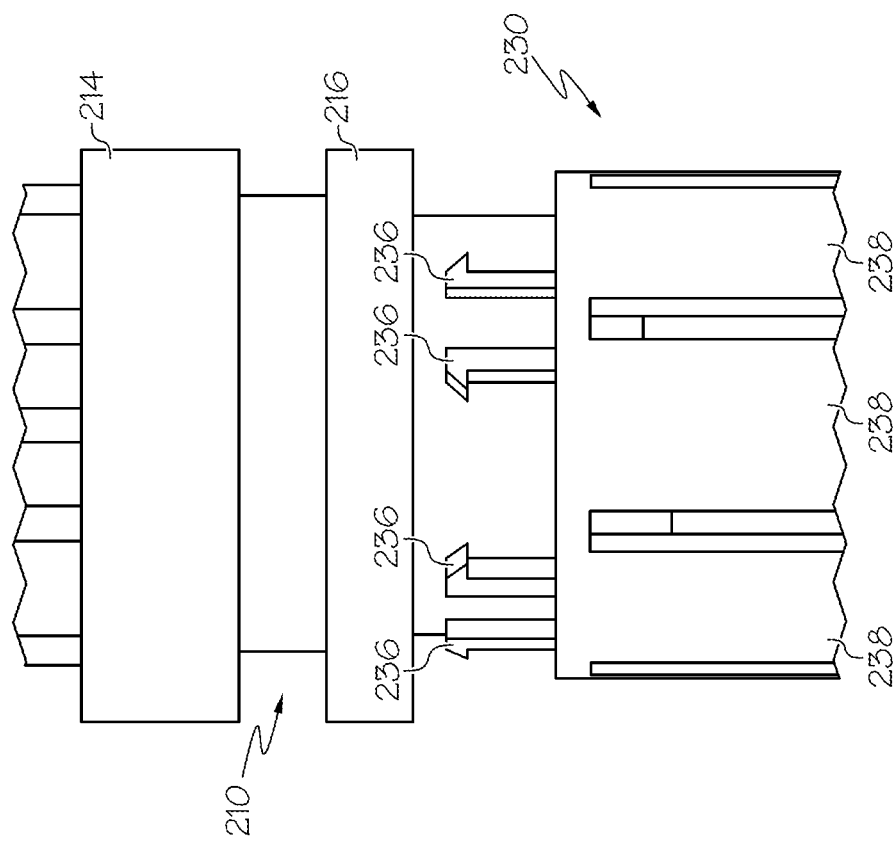

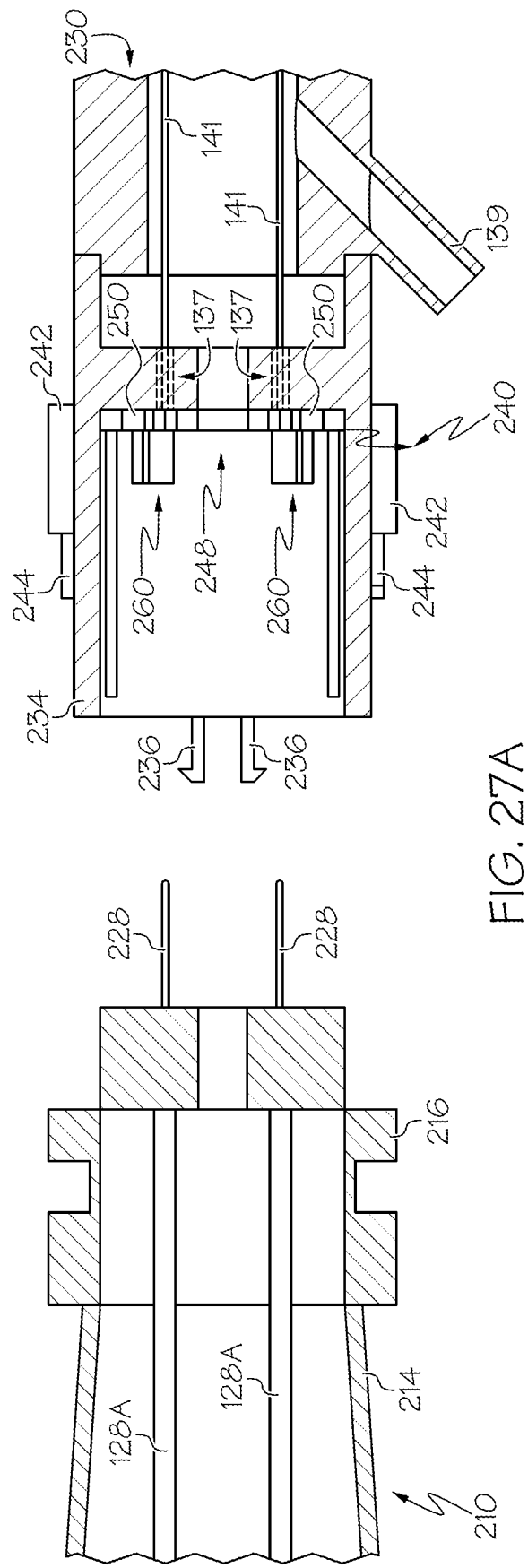
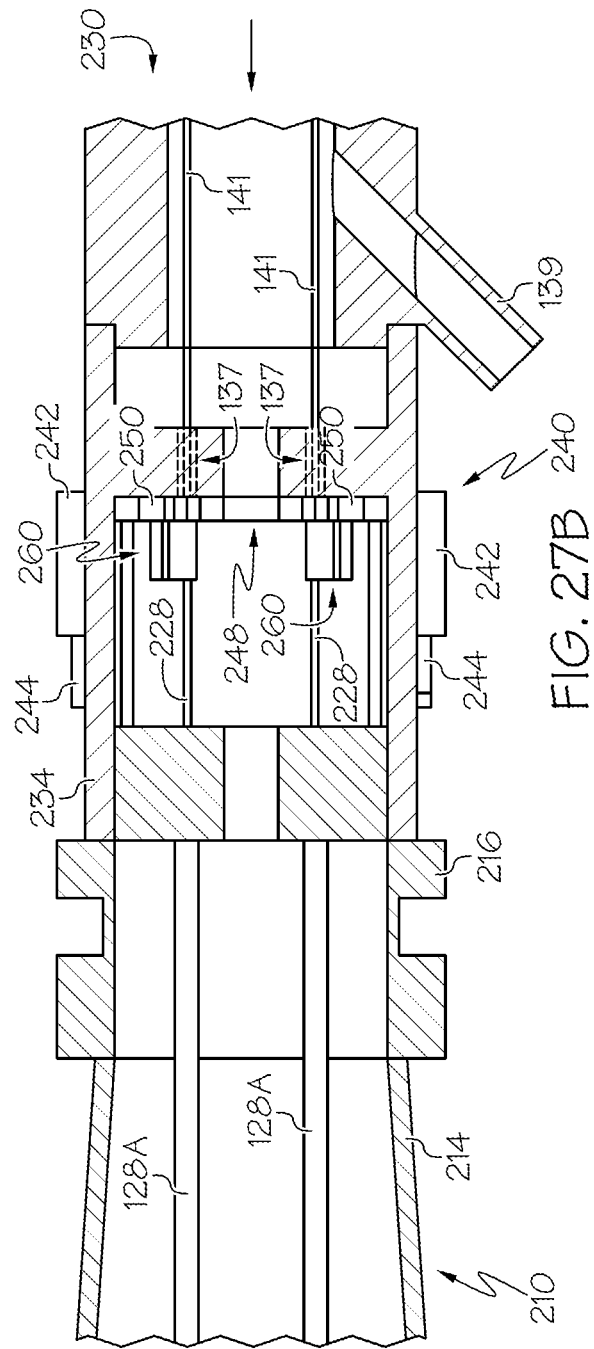
FIG. 27A
FIG. 27B

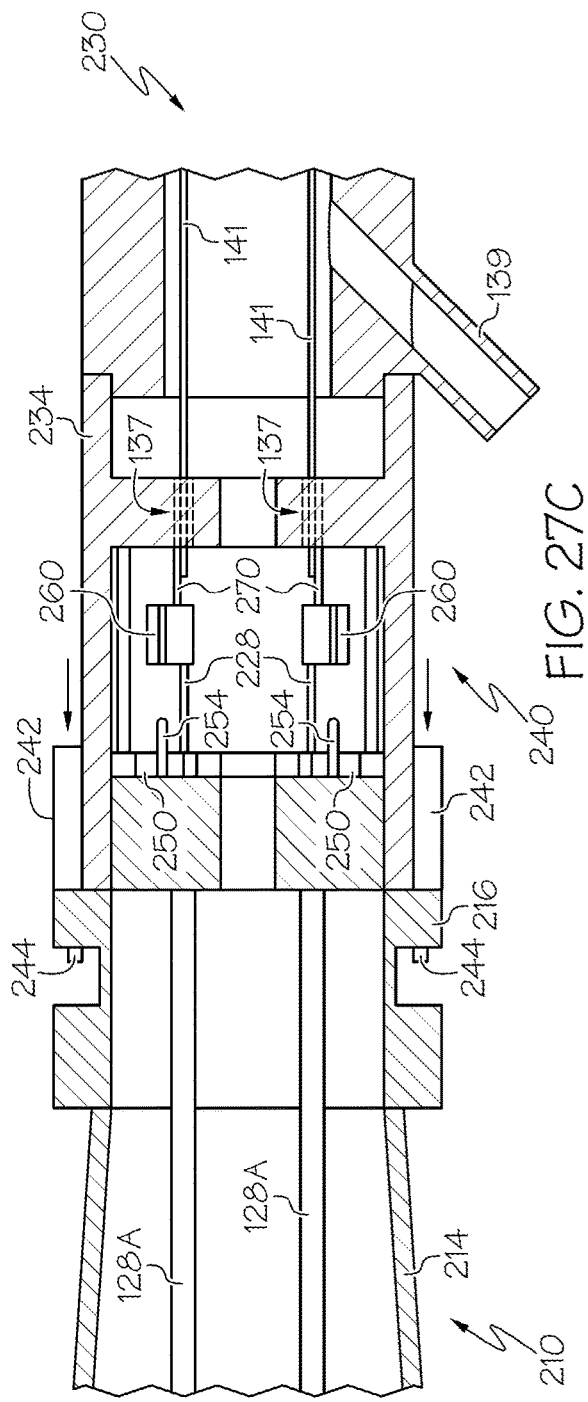
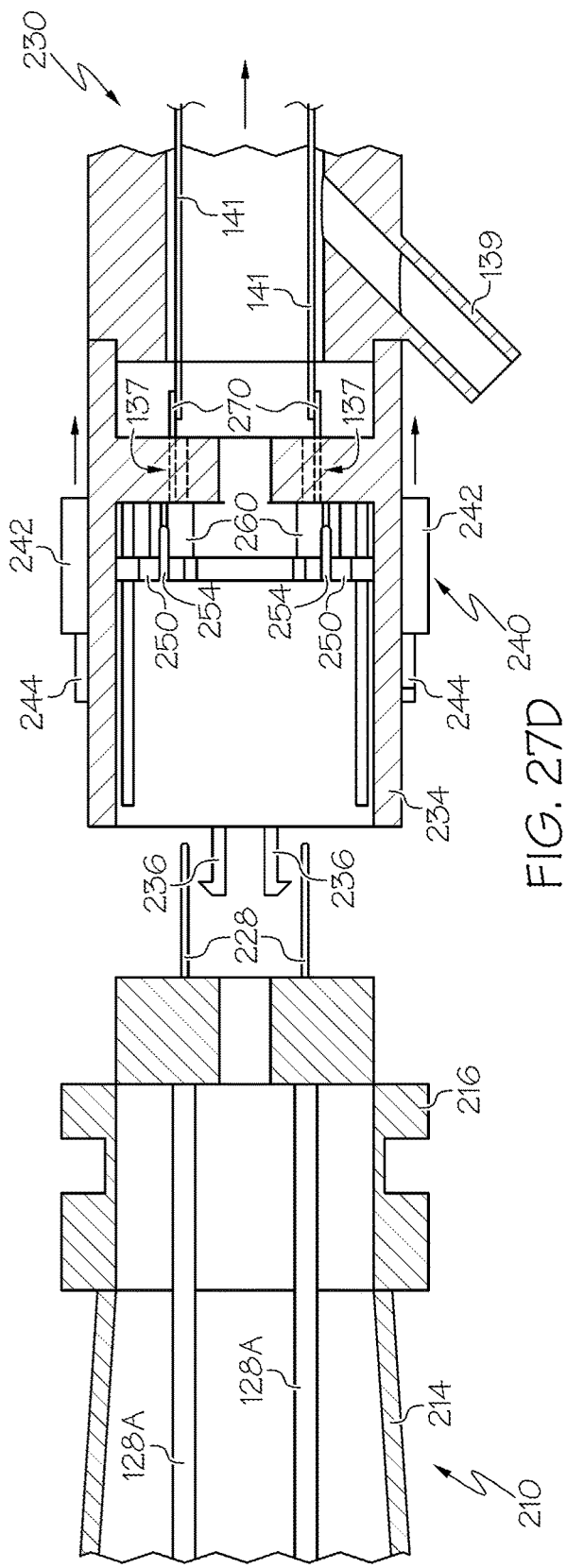
FIG. 27C
FIG. 27D

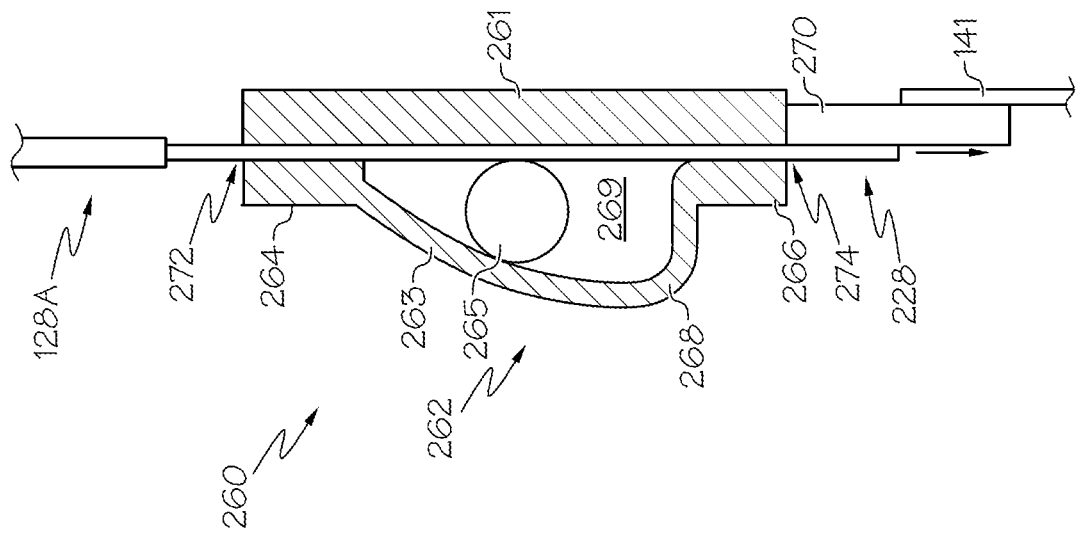
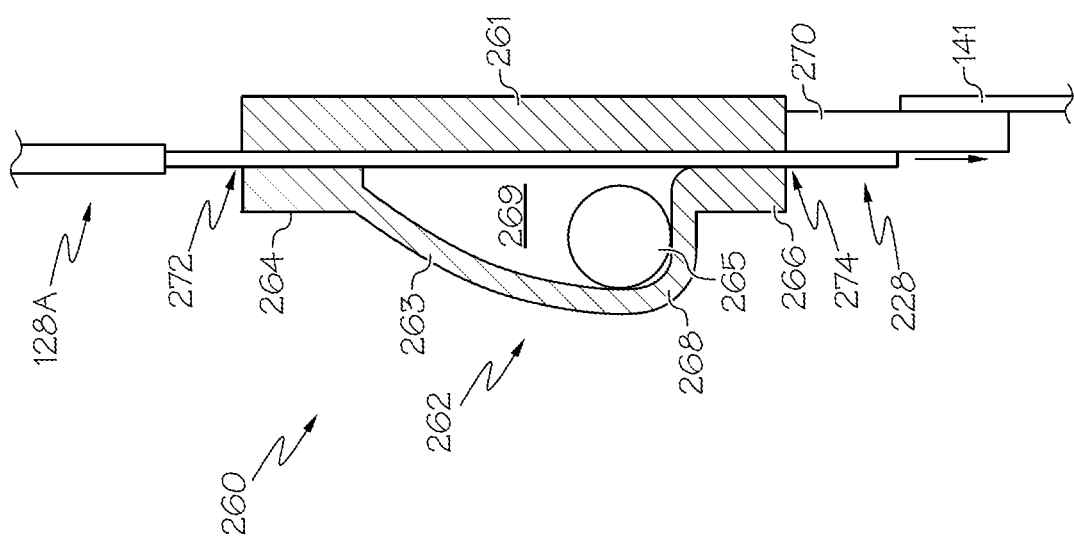

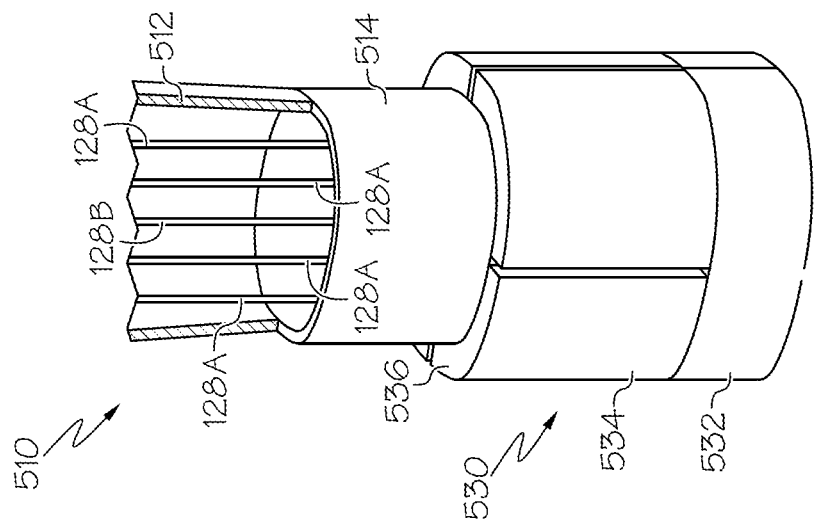
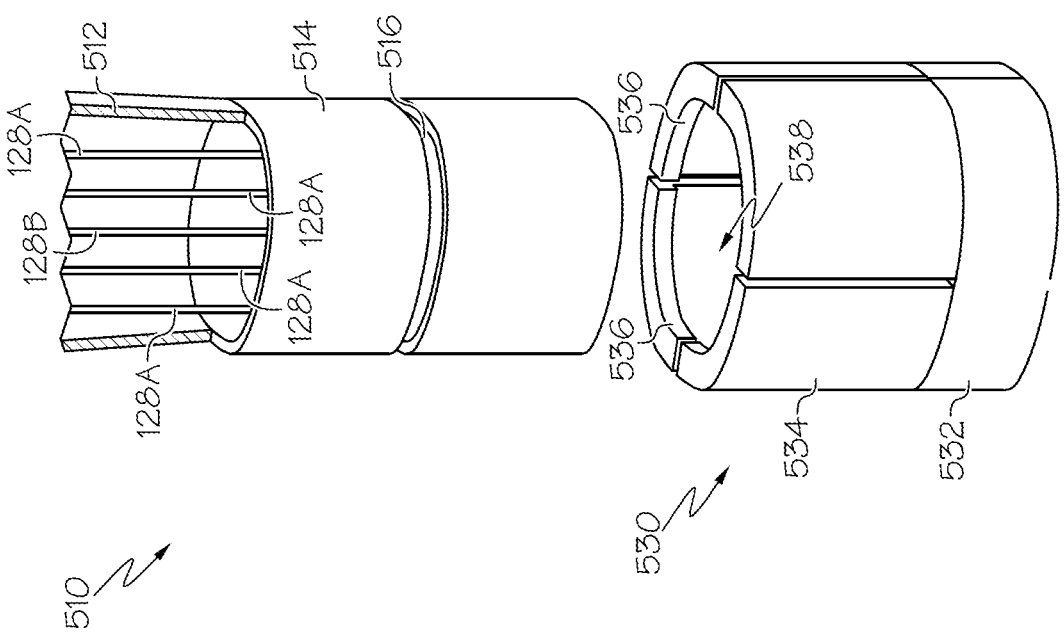

MODULAR MEDICAL DEVICES AND METHODS OF USING THE SAME

CROSS-REFERENCE TO RELATED APPLICATIONS

This application claims the benefit of priority of U.S. Provisional Patent Application No. 63/151,336, filed Feb. 19, 2021, the entirety of which is incorporated herein by reference.

TECHNICAL FIELD

Various aspects of the disclosure relate generally to modular medical systems, devices, and related methods. Examples of the disclosure relate to systems, devices, and related methods for assembling and disassembling components of a modular device, among other aspects.

BACKGROUND

Certain medical devices may be utilized in numerous procedures for treating multiple patients. Prior to reuse, such medical devices may undergo extensive sterilization and/or reprocessing procedures to safely prepare the device for use in a subsequent procedure. However, despite extensive cleaning measures, cross-contamination between patients may still occur from the reuse of medical devices across multiple procedures, thereby resulting in possible infection and other post-procedure complications for the patient. Disposable medical devices may be employed in lieu of reusable medical devices, however, providing for a single use of components may result in increased costs. Medical devices that may be reusable or disposable to provide a balance between minimizing contamination and saving on costs may be limited.

SUMMARY

Aspects of the disclosure relate to, among other things, systems, devices, and methods for a modular medical device including disposable and reusable components, among other aspects. Each of the aspects disclosed herein may include one or more of the features described in connection with any of the other disclosed aspects.

According to an example, a medical device includes a first body including a first actuation wire having a first connector that extends outwardly from the first body; and a second body including: a second actuation wire having a second connector that is disposed within the second body; wherein the first connector is configured to engage the second connector in response to the second body mating with the first body, and to deform the second connector in response to the first body disengaging the second body.

Any of the medical devices described herein may include any of the following features. The first connector includes a plug having a base and a tip, and the second connector includes a barb having an opening and an internal cavity sized to receive the tip through the opening; wherein the base is configured to engage the barb to form a stop between the plug and the barb. The second connector includes a maximum force tolerance, and the first connector is configured to deform the second connector when the first actuation wire applies a force to the first connector that exceeds the maximum force tolerance. The second actuation wire moves relative to the second body in response to the first actuation wire moving relative to the first body. The second connector is fixed to a port of the second body; and wherein the first actuation wire is configured to remove the second connector from the port in response to the first connector engaging the second connector and moving relative to the first body. The second connector is configured to expand when removed from the port, such that the second connector is inhibited from reentering the port. The first body includes a first fluidics port, and the second body includes a second fluidics port that mates with the first fluidics port when the second body mates with the first body. A seal is formed between the first fluidics port and the second fluidics port when the second body mates with the first body at a plurality of axial positions. The second body includes a latch that is configured to engage the first body to fix an axial position of the first body relative to the second body. The second connector includes a housing having a ball bearing that is movable within the housing between a locked position and an unlocked position. The first connector is configured to move the ball bearing within the housing when the second body mates with the first body. The ball bearing is configured to allow movement of the first connector through the housing when in the unlocked position, and inhibit movement of the first connector through the housing when in the locked position. The housing defines a cavity having a narrowed portion and a widened portion that is wider than the narrowed portion; and wherein the ball bearing is positioned within the cavity adjacent to the wider portion when in the unlocked position, and adjacent to the narrowed portion when in the locked position. The first body includes a distal end having a first asymmetric profile, and the second body includes a proximal end having a second asymmetric profile corresponding to the first asymmetric profile. The second body is configured to mate with the first body in a first orientation when the first asymmetric profile is aligned with the second asymmetric profile, and inhibit mating with the first body in a second orientation when the first asymmetric profile is misaligned with the second asymmetric profile.

According to another example, a medical device includes a handle including: a first body; a first actuation wire; and a first connector coupled to the first actuation wire, wherein the first connector is movable relative to the first body in response to movement of the first actuation wire; and a distal portion including: a second body; a second actuation wire; and a second connector coupled to the second actuation wire, wherein the second connector is movable relative to the second body in response to movement of the second actuation wire; wherein the handle is configured to move the first actuation wire and the second actuation wire when the handle is mated with the distal portion and the first connector is engaged with the second connector; and wherein the second connector is configured to deform when the handle is disengaged from the distal portion.

Any of the medical devices described herein may include any of the following features. The handle is configured to move the first connector and the second connector relative to the second body when the handle is mated with the distal portion and the first connector is engaged with the second connector. The distal portion includes a movable latch that engages the handle to secure the first body to the second body; and wherein the movable latch is at least partially deformed in response to engaging the first body. Further including a ring movably coupled to the distal portion, and configured to engage the handle when the handle is mated with the distal portion; wherein the ring is configured to couple the first connector with the second connector, and apply tension to the first actuation wire and the second actuation wire.

According to a further example, a medical device includes a first body including: a first actuation wire; a first connector coupled to the first actuation wire and extending distally from the first body; and a fluid channel; a second body including: a second actuation wire; a second connector coupled to the second actuation wire; and a fluid tube extending proximally from the second body; wherein the first connector is configured to engage the second connector, and the fluid channel is configured to mate with the fluid tube, in response to the second body mating with the first body; and wherein the first connector is configured to alter the second connector so that the second connector cannot engage the first connector, and the fluid channel is configured to disengage with the fluid tube, in response to the first body disengaging from the second body.

According to a further example, a modular endoscope includes a handle; a body removably coupled to the handle; a flexible tube extending distally from the body; and an umbilicus removably coupled to the handle; wherein the umbilicus and the flexible tube are in fluid communication with one another when the handle and the body are coupled to one another; such that the umbilicus is configured to provide fluid delivery and suction through the flexible tube when the handle is coupled to the body; and wherein the fluid communication between the umbilicus and the flexible tube is permanently removed when the handle and the body are decoupled from one another, such that reattachment of the body and the handle is inhibited.

It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary aspects of the disclosure and together with the description, serve to explain the principles of the disclosure.

FIG. 5 is a partial perspective view of the reusable handle of the medical device of FIG. 1, the reusable handle including fluidics ports, according to aspects of this disclosure;

FIG. 6 is a partial perspective view of the reusable handle of the medical device of FIG. 1, the reusable handle including first connectors, according to aspects of this disclosure;

FIG. 7 is a partial perspective view of the disposable portion of the medical device of FIG. 1, the disposable portion including fluidics tubes, according to aspects of this disclosure;

FIG. 8 is a partial perspective view of the reusable handle being aligned within the disposable portion of the medical device of FIG. 1, with the fluidics ports of the reusable handle aligned with the fluidics tubes of the disposable portion, according to aspects of this disclosure;

FIG. 9 is a partial side view of the reusable handle aligned for receipt with the disposable portion of the medical device of FIG. 1, with the first connectors of the reusable handle aligned with the second connectors of the disposable portion, according to aspects of this disclosure;

FIG. 10 is a partial cross-sectional view of the reusable handle partially received in the disposable portion of the medical device of FIG. 1, with the fluidics tubes of the disposable portion received within the fluidics ports of the reusable handle, according to aspects of this disclosure;

FIG. 19 is a partial perspective view of a locking mechanism of the disposable portion of the medical device of FIG. 1, according to aspects of this disclosure;

FIG. 20 is a partial side view of the reusable handle removed from the disposable portion of the medical device of FIG. 1, with the first connectors of the reusable handle disengaged from the second connectors of the disposable portion, according to aspects of this disclosure;

FIG. 21 is a partial cross-sectional view of another exemplary medical device including a reusable handle and a disposable portion, according to aspects of this disclosure;

FIG. 22 is a perspective view of a locking ring of the medical device of FIG. 21, according to aspects of this disclosure;

FIG. 23 is a perspective view of the locking ring of FIG. 22, according to aspects of this disclosure;

FIG. 26A is a partial side view of the disposable portion disengaged from the reusable handle of the medical device of FIG. 21, according to aspects of this disclosure;

FIG. 26B is a partial side view of the disposable portion engaged to the reusable handle of the medical device of FIG. 21, according to aspects of this disclosure;

FIG. 27A is a partial cross-sectional view of the reusable handle aligned for receipt within the disposable portion of the medical device of FIG. 21, according to aspects of this disclosure;

FIG. 27B is a partial cross-sectional view of the reusable handle received within the disposable portion of the medical device of FIG. 21, according to aspects of this disclosure;

FIG. 27C is a partial cross-sectional view of the locking ring of FIG. 22 engaged to the reusable handle of the medical device of FIG. 21, according to aspects of this disclosure;

FIG. 27D is a partial cross-sectional view of the locking ring of FIG. 22 disengaged from the reusable handle of the medical device of FIG. 21, and the reusable handle removed from within the disposable portion, according to aspects of this disclosure;

FIG. 28A is a partial perspective view of a connector mechanism of the medical device of FIG. 21, with the connector mechanism in an unlocked state, according to aspects of this disclosure;

FIG. 28B is a partial perspective view of the connector mechanism of FIG. 28A, with the connector mechanism in a locked state, according to aspects of this disclosure;

FIG. 31A is a partial perspective view of another exemplary medical device including a reusable handle and a disposable portion in a decoupled state, according to aspects of this disclosure; and FIG. 31B is a partial perspective view of the reusable handle and the disposable portion of the medical device of FIG. 31A in a coupled state, according to aspects of this disclosure.

DETAILED DESCRIPTION

Figure 1:
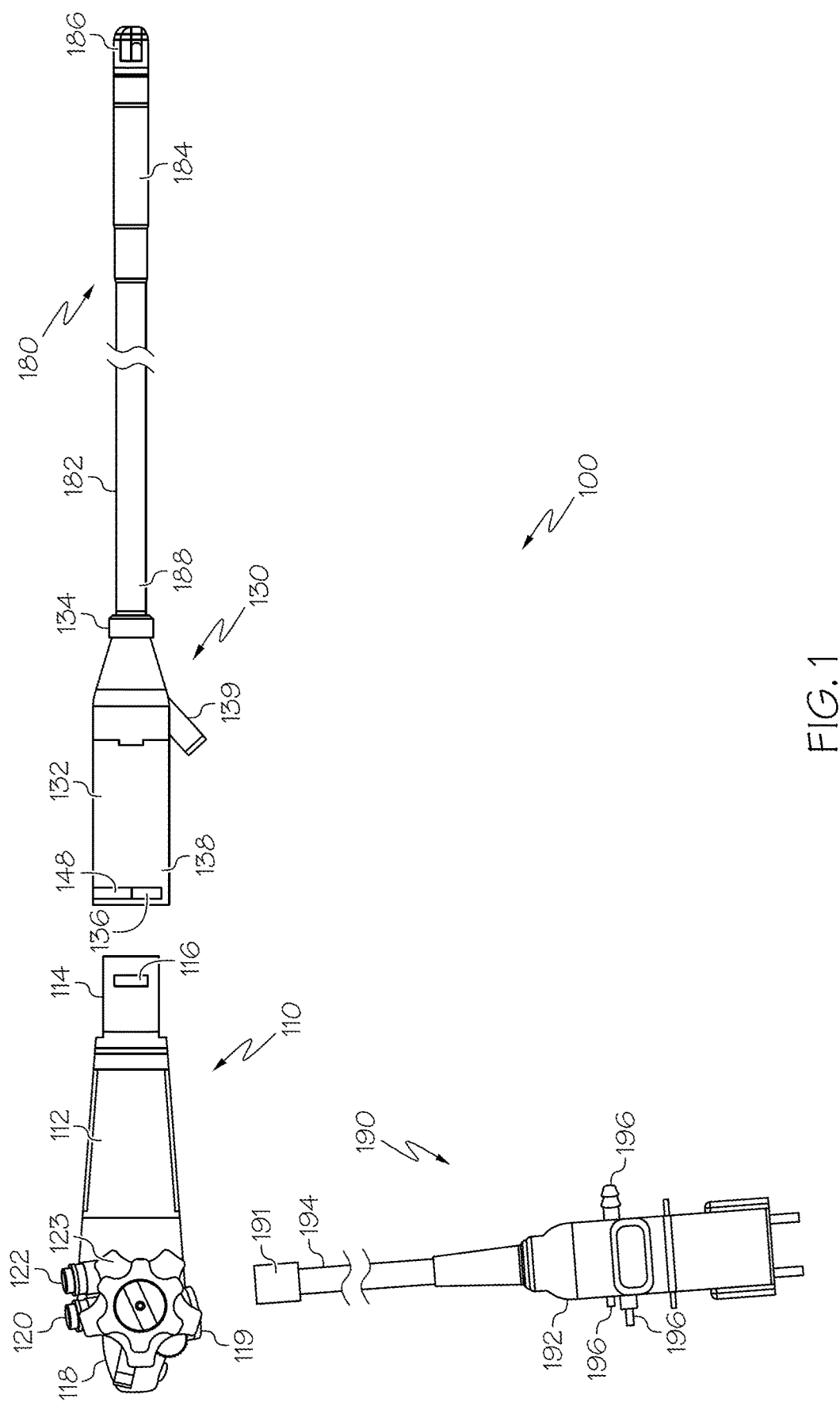
FIG. 1 is a side view of an exemplary medical device including a first (reusable) handle and a second (disposable) portion, according to aspects of this disclosure.

This disclosure relates, in certain aspects, to modular medical devices with reusable and disposable components. In some procedures, reuse of a medical device (e.g., endoscope) that was previously utilized in a prior procedure for a same or different patient may be common after the device has undergone sterilization and/or reprocessing measures. Such measures may be generally costly and imperfect as subsequent patients may be at an increased risk to sustain ailments (e.g., infection) resulting from cross-contamination of the device from a prior medical procedure. Employing single-use medical devices may minimize instances of utilizing contaminated devices in subsequent procedures, however, disposal of single-use devices may not provide an efficient balance of saving costs and minimizing contamination.

Examples of the disclosure include systems, devices, and methods for a modular medical device including a reusable handle and a disposable portion for treating a target treatment site within a subject (e.g., patient). The reusable handle may be positioned external to the target treatment site during a procedure, such that contamination of the reusable handle may be minimized, thereby allowing for the reusable handle to be reutilized in subsequent procedures with a reduced risk of cross-contamination between patients. At least part of the disposable portion may be received within the target treatment site during a procedure and disassembled from the reusable handle upon completion of the procedure, thereby allowing for the disposal of the disposable portion to minimize contamination of subsequent patients. In examples, accessing a target treatment site may include endoluminal placement of the medical device into the patient, such as through an anatomical passageway via a natural orifice. The orifice can be, for example, the nose, mouth, or anus, and the placement can be in any portion of the GI tract, including the esophagus, stomach, duodenum, large intestine, or small intestine. Placement also can be in other organs or other bodily spaces reachable via the GI tract, other body lumens, or openings in the body. This disclosure is not limited to any particular medical procedure or treatment site within a body.

Examples of the disclosure may relate to devices and methods for performing various medical procedures and/or treating portions of the large intestine (colon), small intestine, cecum, esophagus, any other portion of the gastrointestinal tract, and/or any other suitable patient anatomy (collectively referred to herein as a "target treatment site"). As mentioned above, this disclosure is not limited to any specific medical device or method, and aspects of the disclosure may be used in connection with any suitable medical tool and/or medical method, at any suitable site within the body.

Reference will now be made in detail to aspects of the disclosure, examples of which are illustrated in the accompanying drawings. Wherever possible, the same or similar reference numbers will be used through the drawings to refer to the same or like parts. The term "distal" refers to a portion farthest away from a user when introducing a device into a patient. By contrast, the term "proximal" refers to a portion closest to the user when placing the device into the subject. As used herein, the terms "comprises," "comprising," or any other variation thereof, are intended to cover a non-exclusive inclusion, such that a process, method, article, or apparatus that comprises a list of elements does not necessarily include only those elements, but may include other elements not expressly listed or inherent to such process, method, article, or apparatus. The term "exemplary" is used in the sense of "example," rather than "ideal." As used herein, the terms "about," "substantially," and "approximately," indicate a range of values within +/−10% of a stated value.

FIG. 1 shows an exemplary medical device 100 in accordance with an example of this disclosure. Medical device 100 may include a first (reusable) handle 110, a second (disposable) portion 130, and a (disposable) umbilicus assembly 190. Medical device 100 may have a modular configuration such that first handle 110 and second portion 130 may be selectively coupled and decoupled from one another, and first handle 110 and umbilicus assembly 190 may be selectively coupled and decoupled from one another. First handle 110 may be configured such that first handle 110 may be reusable across multiple procedures, and second portion 130 and/or umbilicus assembly 190 may be configured such that second portion 130 and/or umbilicus assembly 190 may be disposable after a single use. Accordingly, at least a portion of medical device 100 may be disassembled and discarded after use in a procedure. In some embodiments, umbilicus assembly 190, like first handle 110, may be reusable across multiple procedures.

First handle 110 may include a body 112 having a longitudinal length defined between a distal end 114 and a proximal end 118. First handle 110 may include a groove 116 disposed on at least a side surface of body 112 at distal end 114, and distal end 114 may be sized and shaped to be received within second portion 130. First handle 110 may include at least a first button 120, a second button 122, and a plurality of knobs 123 at proximal end 118. As described further herein, first button 120 and second button 122 may be configured to selectively establish fluid communication between the one or more components of medical device 100, and the plurality of knobs 123 may be configured to actuate one or more components of medical device 100.

Still referring to FIG. 1, first handle 110 may include a port 119 at proximal end 118 that may be configured to receive one or more components of umbilicus assembly 190, such as, for example, an umbilicus 194. Umbilicus assembly 190 may include a distal umbilicus connector 191, a proximal umbilicus connector 192, and umbilicus 194 coupled to umbilicus connectors 191, 192. Umbilicus 194 may be configured to fluidly and/or electrically couple distal umbilicus connector 191 to first handle 110 and second portion 130 via a connection with first handle 110 at port 119.

Umbilicus connectors 191, 192 and umbilicus 194 may include one or more fluid channels (not shown) that are configured to fluidly couple corresponding fluidics tubes of first handle 110 and second portion 130 with one or more fluid sources (not shown). For example, umbilicus assembly 190 may include at least one or more of a suction channel, a pressurized air channel, and a water channel extending through umbilicus connectors 191, 192 and umbilicus 194. The one or more fluid sources (e.g., a negative pressure medium source, a water supply source, a pressurized air source, etc.) may be coupled to umbilicus assembly 190 via umbilicus connector 192, and particularly at one or more nozzles 196 on umbilicus connector 192. As described in detail below, first button 120 and second button 122 may be configured to selectively connect and/or disconnect the one or more fluid channels of umbilicus assembly 190 with the corresponding fluidics tubes of first handle 110.

Umbilicus connectors 191, 192 and umbilicus 194 may further include one or more electronic cables (not shown) that are configured to electrically couple to corresponding electronic cables of first handle 110. In some embodiments, first handle 110 may first electronic cables (not shown) disposed within body 112, and having an electrical connector terminating at, and accessible from, port 119. The first electronic cables may be coupled to second electronic cables disposed within umbilicus connectors 191, 192 by connecting the electrical connectors of the first electronic cables to corresponding electrical connectors of the second electronic cables. For example, the electrical connectors of the first and second electronic cables may be manually connected to one another by a user of medical device 100. In other examples, the corresponding electrical connectors may automatically mate with one another when first handle 110 is coupled to umbilicus assembly 190. In some embodiments, one or more of the fluid connections and/or electronic cable connectors may be altered, deformed, broken, and/or rendered unsuitable for further use upon disengagement of first handle 110 from umbilicus assembly 190.

Still referring to FIG. 1, second portion 130 may include a body 132 having a longitudinal length defined between a distal end 134 and a proximal end 138. Second portion 130 may include a slot 136 disposed on at least a side surface of body 132 at proximal end 138, and a port 139 disposed on at least another side surface of body 132 adjacent to distal end 134. Second portion 130 may include a locking mechanism 148 movably coupled to body 132 at proximal end 138. Slot 136 may be sized and shaped to receive locking mechanism 148 therein. In the embodiment, locking mechanism 148 may include a latch that is pivotable relative to body 132 and receivable through slot 136. As described in further detail herein, locking mechanism 148 may be configured to engage first handle 110 through slot 136 to secure second portion 130 to first handle 110. Port 139 may be sized, shaped, and configured to receive one or more devices (not shown) into second portion 130, such as, for example, a sample collection device, a biopsy forceps, a grasper, or any other therapeutic or diagnostic tool. With port 139 located on second portion 130 (as opposed to first handle 110), it should be appreciated that fewer devices may be traversed through body 112, thereby minimizing a wear and tear of first handle 110 (i.e., the reusable handle).

Medical device 100 may include a (disposable) tube assembly 180 coupled to second portion 130 at distal end 134. Tube assembly 180 may include a shaft 182 having a longitudinal length defined between a distal end 184 and a proximal end 188. Proximal end 188 may be coupled to distal end 134 such that shaft 182 may extend distally from second portion 130. Distal end 184 may include a distal tip 186 having one or more tools, electronics, or other parts. For example, distal tip 186 may include one or more imaging devices, illumination devices, sensors, movable elevator ramps, and/or egress openings for one or more channels (not shown) of shaft 182. Shaft 182 may have a flexible body, and may include one or more channels (not shown) extending between proximal end 188 and distal end 184. For example, shaft 182 may include a working channel for receiving ancillary tools (e.g., a guidewire), a suction channel, a water channel, a pressurized air channel, and more.

Figure 2:
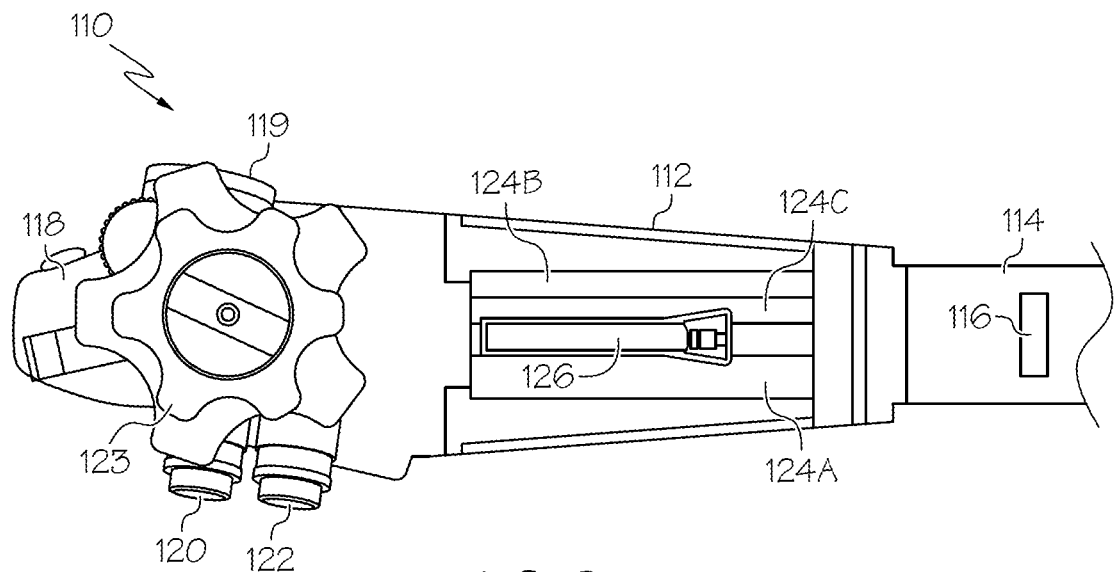
FIG. 2 is a partial side view of an interior of the reusable handle of the medical device of FIG. 1, according to aspects of this disclosure.

Referring now to FIG. 2, first handle 110 is schematically depicted with a side surface of body 112 partially omitted, thereby illustrating an internal cavity of body 112 housing a first fluidics tube 124A, a second fluidics tube 124B, and a third fluidics tube 124C (collectively referred to herein as "fluidics tubes 124"). For example, first fluidics tube 124A may include a suction tube that may be fluidly coupled to a negative pressurized medium source via umbilicus assembly 190. Second fluidics tube 124B may include a water tube that may be fluidly coupled to a water source via umbilicus assembly 190. Third fluidics tube 124C may include an air tube that may be fluidly coupled to an air source via umbilicus assembly 190. In other embodiments, one or more of fluidics tubes 124 may be coupled to various other suitable devices via umbilicus assembly 190.

Fluidics tube 124A may be configured to receive one or more materials (e.g., biological matter, solid particulates, fluid, etc.) from a target treatment site during use of medical device 100 in a procedure. Fluidics tube 124B and/or fluidics tube 124C may be configured to deliver one or more materials to a target treatment site, such as, for example, water and/or pressurized air, respectively. Fluidics tubes 124 may have one or more characteristics that are configured to facilitate and optimize mechanical cleaning of the fluidics tubes 124 after use in a procedure. For example, fluidics tubes 124 may have a linear and/or straight configuration relative to the longitudinal length of body 112. Further, each of the fluidics tubes 124 may have a relatively short length, such as a length that is equal to or less than the longitudinal length of body 112, thereby increasing an accessibility into each of the fluidics tubes 124 for cleaning.

One or more of fluidics tubes 124 may be formed of a rigid material, including, for example, a metal, metal alloy, autoclave-safe thermoplastics, and more. In this instance, fluidics tubes 124 may be operable for cleaning via autoclave sterilization processes while minimizing degradation of fluidics tubes 124. Stated differently, fluidics tubes 124 may be rigid to increase a durability for fluidics tubes 124 to undergo numerous cleaning measures and/or be scratch resistant. With first handle 110 being a reusable component of medical device 100, providing rigid fluidics tubes 124 may allow first handle 110 to be reprocessed for multiple uses.

Figure 3:
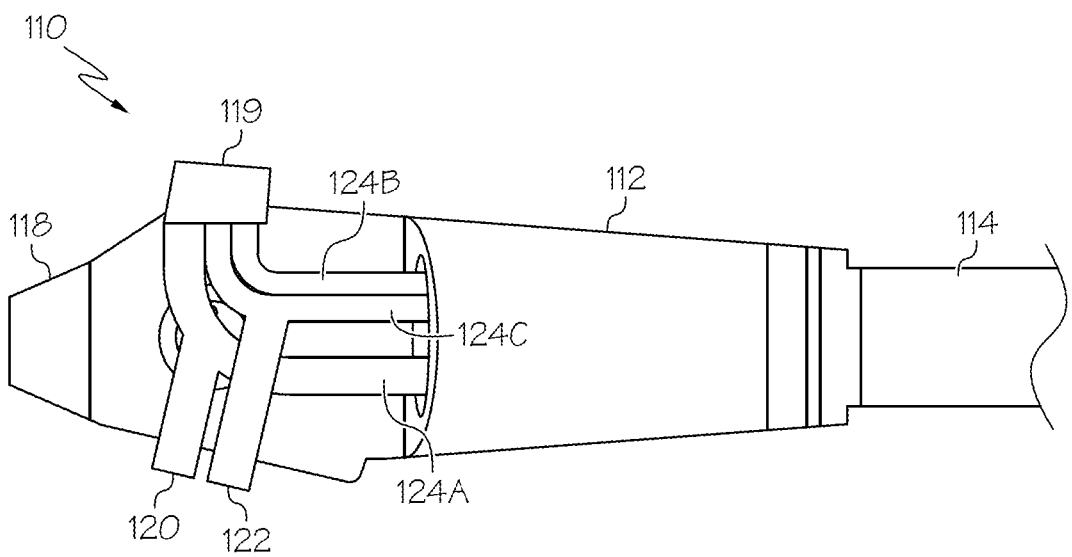
FIG. 3 is a partial side view of an interior of the reusable handle of the medical device of FIG. 1, according to aspects of this disclosure.

Still referring to FIG. 2, first handle 110 may further include an elevator mechanism 126 disposed within the internal cavity of body 112. Elevator mechanism 126 may be coupled to one or more actuation lines (FIG. 4), and may be configured to actuate (e.g., move, deflect, pivot) a device at distal tip 186 (e.g., an elevator) in response to movement of one or more knobs 123. In some embodiments, elevator mechanism 126 may include a slot or opening that is sized, shaped, and configured to receive an elevator actuation cable. As seen in FIG. 3, first button 120 may be coupled to first fluidics tube 124A, and second button 122 may be coupled to second fluidics tube 124B and third fluidics tube 124C. Each of first button 120 and second button 122 may be configured to control a sealing mechanism (e.g., a valve, a septum, etc.) disposed between buttons 120, 122 and its corresponding fluidics tubes 124. Accordingly, first button 120 and second button 122 may be configured to selectively open and close the sealing mechanism to establish fluid communication between fluidics tubes 124 and the fluid channels of umbilicus assembly 190.

Figure 4:
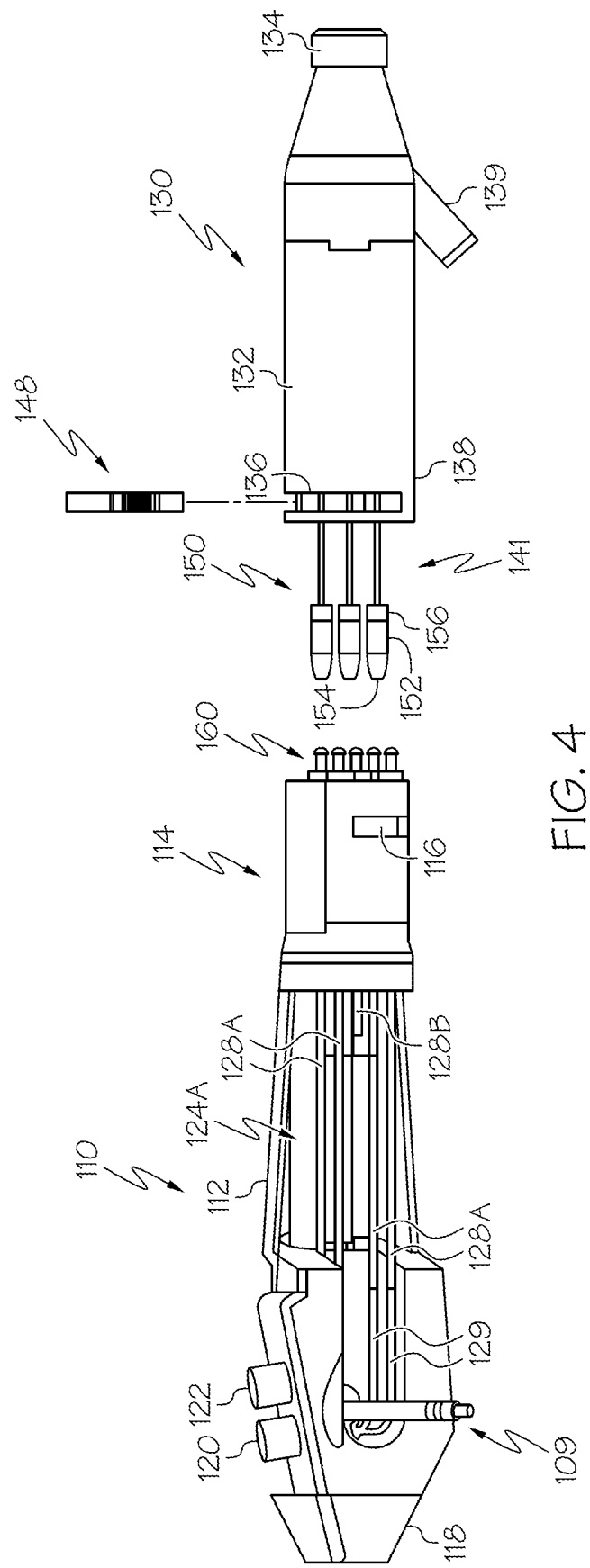
FIG. 4 is a partial exploded view of an interior of the reusable handle and the disposable portion of the medical device of FIG. 1, according to aspects of this disclosure.

Referring now to FIG. 4, first handle 110 is schematically depicted with a side surface of body 112 partially omitted, thereby illustrating the internal cavity of body 112 housing one or more first actuation lines 128A (e.g., pull wires) and second actuation lines 128B (e.g., push-pull wires) (collectively referred to herein as "actuation lines 128"). Actuation lines 128 may be movable (e.g., translatable, etc.) relative to first handle 110. For example, one or more of the plurality of first actuation lines 128A may be movably coupled to one another via at least one drive cable 129. Movement of at least one first actuation line 128A may provide for a corresponding movement of at least another first actuation line 128A via drive cable 129 coupled therebetween. In some examples, drive cable 129 may be formed of a rigid material, such as, for example, a metal, metal alloy, and more.

First handle 110 may further include one or more articulation shafts 109 coupled to drive cables 129 via one or more drive pulleys (not shown) disposed about an exterior of drive cables 129. In the embodiment, articulation shafts 109 may be movably coupled to the plurality of knobs 123 (see FIGS. 1-2) such that actuation (e.g., movement) of knobs 123 may provide for a corresponding movement of articulation shafts 109, drive cables 129, and the plurality of first actuation lines 128A. Second actuation line 128B may be coupled to one or more of the plurality of knobs 123 and articulation shafts 109 via elevator mechanism 126. Each actuation line 128 may include a distal end having a plug connector 160 (e.g., a first connector) that extends outward from the internal cavity of body 112 at distal end 114. The plurality of plug connectors 160 may be rigid and formed of a rigid material, such as, for example, a metal, an autoclave material, a hard plastic, and/or various suitable high strength resins.

As seen in FIG. 4, second portion 130 may include a plurality of barb connectors 150 (e.g., a second connector) that may be sized, shaped, and configured to interact with the plurality of plug connectors 160. Each of the plurality of barb connectors 150 may include a body 152 having a longitudinal length defined between a proximal end 154 and a distal end 156. Body 152 may be formed of a flexible material that is relatively softer than the material of the plurality of plug connectors 160, such as, for example, an elastomer, polyethylene, plastic, and/or various suitable low strength resins, making body 152 flexible relative to plug connectors 160.

Each proximal end 154 may include a proximal opening that is sized and shaped to receive at least a portion of a corresponding plug connector 160. Each body 152 of the plurality of barb connectors 150 may be coupled to a wire or a cable 141 that is movable relative to second portion 130 in response to a corresponding movement of barb connectors 150. Cables 141 may extend through body 132 and into shaft 182, and may be coupled to distal end 184 such that movement of cables 141 relative to second portion 130 may provide for movement of distal end 184 relative to proximal end 188. Cables 141 may be formed of a rigid material, such as, for example, a metal, so that cables 141 do not elongate but may be flexible. In the example, movement of distal end 184 and/or distal tip 186 (e.g., left and right, up and down, etc.) relative to proximal end 188 may be caused by rotation of knobs 123, which thereby turns articulation shafts 109 and the one or more drive pulleys coupled thereto. In response, drive cables 129 and articulation lines 128A may translate relative to first handle 110, thereby causing translation of cables 141 relative to second portion 130. Second portion 130 may include four cables 141 corresponding to four articulation lines 128A within first handle 110 for articulating distal tip 186.

Referring now to FIG. 5, first handle 110 may include one or more electronic cable ports 111, fluidics ports 115, and actuation ports 117 at distal end 114. In the embodiment, distal end 114 may include a pair of electronic cable ports 111 for housing one or more electronic cables therethrough. In some embodiments, first handle 110 may first electronic cables (not shown) disposed within body 112, and having an electrical connector terminating at the distal end 114 and accessible at cable ports 111. The first electronic cables may be coupled to third electronic cables disposed within second portion 130 by connecting the electrical connectors of the first electronic cables to corresponding electrical connectors of the third electronic cables. For example, the electrical connectors of the first and third electronic cables may be manually connected to one another by a user of medical device 100. In other examples, the corresponding electrical connectors may automatically mate with one another when first handle 110 is coupled to second portion 130. In some embodiments, the electronic cable connectors may be altered, deformed, broken, and/or rendered unsuitable for further use upon disengagement of first handle 110 from second portion 130.

Distal end 114 may include a first fluidics port 115A, a second fluidics port 115B, and a third fluidics port 115C (collectively referred to herein as "fluidics ports 115"). First fluidics port 115A may be in fluid communication with first fluidics tube 124A, second fluidics port 115B may be in fluid communication with second fluidics tube 124B, and third fluidics port 115C may be in fluid communication with third fluidics tube 124C. Distal end 114 may further include a plurality of actuation ports 117, each of which may be configured to receive at least one of the plurality of actuation lines 128.

Distal end 114 may have a cross-sectional profile that is defined by at least a first exterior sidewall 113A and a second exterior sidewall 113B. Each of first exterior sidewall 113A and second exterior sidewall 1136 may have a size, a shape, and/or a configuration that varies relative to one another. For example, first exterior sidewall 113A may define a smaller surface area and/or lateral width between a top and bottom surface of distal end 114 relative to second exterior sidewall 1136. Collectively, exterior sidewalls 113A, 113B may form an asymmetric shape at distal end 114, thereby providing a keyed column for first handle 110. In this instance, first handle 110 may be received within second portion 130 when first handle 110 is positioned at a particular orientation relative to second portion 130.

With distal end 114 having the asymmetric profile, second portion 130 may be configured to receive first handle 110 when distal end 114 is moved (e.g., rotated) to a particular orientation relative to proximal end 138. As shown and described in detail below, second portion 130 may include a corresponding size, shape, and/or configuration at proximal end 138 (see FIG. 7) that is configured to compliment the asymmetric profile of distal end 114. Accordingly, the keyed column formed at distal end 114 may ensure proper alignment of first handle 110 relative to second portion 130 for assembling each component to one another.

Referring now to FIG. 6, the plurality of actuation lines 128 received in first handle 110 may extend outwardly from distal end 114 via the plurality of actuation ports 117. The plurality of plug connectors 160 may move (e.g., translate) relative to distal end 114 in response to a movement of actuation wires 128 within body 112. Plug connectors 160 may include a body defined by a proximal base 162 and a distal tip 164, with proximal base 162 having a greater, radial cross-sectional dimension than distal tip 164. In the example, proximal base 162 of each actuation wire 128 may have a diameter that is greater than a diameter of actuation ports 117, such that proximal retraction of plug connectors 160 into first handle 110 may be inhibited upon engagement of proximal base 162 with distal end 114. In this instance, an interaction between a distally-directed face of distal end 114 and proximal base 162 may define a hard stop. Distal tip 164 of each actuation wire 128 may have a size that is smaller than the proximal opening at proximal end 154, such that plug connectors 160 may be configured to couple barb connectors 150 in response to distal tip 164 being received through the proximal opening of body 152. It should be appreciated that distal tip 164 may have various suitable shapes, sizes, profiles, and/or configurations. For example, distal tip 164 may have a rounded, filleted, chamfered, and/or other shape.

Referring now to FIG. 7, proximal end 138 may include a keyed opening 140 that is sized, shaped, and configured to receive distal end 114. Keyed opening 140 may be at least partially defined by a first interior sidewall 133A and a second interior sidewall 133B. First interior sidewall 133A may have a smaller surface area and/or lateral width relative to second interior sidewall 133B, and collectively the interior sidewalls 133A, 133B may form an asymmetric opening for second portion 130 at proximal end 138 (i.e., keyed opening 140).

In the example, first interior sidewall 133A may be sized and shaped in association with a size and shape of first exterior sidewall 113A, and second interior sidewall 133B may be sized and shaped in association with second exterior sidewall 113B. Accordingly, keyed opening 140 at proximal end 138, defined by interior sidewalls 133A, 133B, may correspond to the keyed column at distal end 114, as defined by exterior sidewalls 113A, 113B. In this instance, second portion 130 may receive first handle 110 when first exterior sidewall 113A is aligned with first interior sidewall 133A, and second exterior sidewall 113B is aligned with second interior sidewall 133B. Second portion 130 may inhibit receipt of first handle 110 when first exterior sidewall 113A is misaligned with first interior sidewall 133A, and/or second exterior sidewall 113B is misaligned with second interior sidewall 133B.

Still referring to FIG. 7, second portion 130 may include one or more electronic cable ports 131, fluidics ports 135, and actuation ports 137 within keyed opening 140. In the embodiment, proximal end 138 may include a pair of electronic cable ports 131 for receiving one or more electronic cables from electronic cable ports 111 when first handle 110 is coupled to second portion 130. Proximal end 138 may further include a first fluidics port 135A, a second fluidics port 135B, and a third fluidics port 135C (collectively referred to herein as "fluidics ports 135"). First fluidics port 135A may be in fluid communication with first fluidics port 115A when first handle 110 is coupled to second portion 130, thereby fluidly coupling first fluidics tube 124A to second portion 130. Second fluidics port 135B may be in fluid communication with second fluidics port 1156 when first handle 110 is coupled to second portion 130, thereby fluidly coupling second fluidics tube 124B to second portion 130. Third fluidics port 135C may be in fluid communication with third fluidics port 115C when first handle 110 is coupled to second portion 130, thereby fluidly coupling third fluidics tube 124C to second portion 130.

Each of the fluidics ports 135 may include a tubular conduit that extends proximally from proximal end 138 such that fluidics ports 135 may extend at least partially outward from keyed opening 140. Each of the tubular conduits may have a longitudinal length and/or diameter that is sized and shaped for receipt within the corresponding fluidics ports 115 when second portion 130 is coupled to first handle 110. In some embodiments, each fluidics port 135 may have one or more sealing mechanisms 146 (e.g., an O-ring) disposed along at least an exterior surface of the tubular conduit for forming a seal against an interior surface of fluidics ports 115 (see FIG. 8).

Still referring to FIG. 7, proximal end 138 may include a plurality of actuation ports 137, each of which may include a stop wall 137A. Each of the plurality of actuation ports 137 may be configured to receive at least one of the plurality of barb connectors 150, and stop wall 137A may define an interface that receives distal end 156 of each barb connector 150. Stop walls 137A may have a diameter that is sized relatively smaller than a cross-sectional dimension of body 152, such that barb connectors 150 may be inhibited from extending distally through actuation ports 137 by stop walls 137A. With distal ends 156 of barb connectors 150 coupled to cables 141, it should be appreciated that cables 141 may be received through actuation ports 137.

As best seen in FIG. 8, proximal end 138 may include a pair of latch openings 147 along a side surface of body 132 for coupling locking mechanism 148 to second portion 130. In the example, locking mechanism 148 may be attached via a hinge and ball joint (not shown) positioned between the pair of latch openings 147. In this instance, locking mechanism 148 (e.g., a latch, a lever, etc.) may be movable relative to proximal end 138 between an open position and a closed position about latch openings 147. As described in detail herein, locking mechanism 148 may be configured to generate an interference between second portion 130 and first handle 110 to fix an axial position of first handle 110 relative to second portion 130.

In the example, the tubular conduits of each fluidics port 135 may include a pair of sealing mechanisms 146 (e.g., O-rings) disposed along an exterior surface of the tubular conduits and at a proximal end of fluidic port 135. The pair of sealing mechanisms 146 may be configured to form a seal between first handle 110 and second portion 130 when the plurality of fluidics ports 135 are received within the plurality of fluidics ports 115.

Referring to FIG. 9, and according to an exemplary method of using medical device 100, first handle 110 may be coupled to second portion 130 in response to aligning distal end 114 with proximal end 138. In the embodiment, the keyed column defined by exterior sidewalls 113A, 113B may be aligned with keyed opening 140, as defined by interior sidewalls 133A, 133B, to permit receipt of distal end 114 within proximal end 138. It should be appreciated that second portion 130 may inhibit receipt of distal end 114 within proximal end 138 when the keyed column of first handle 110 is misaligned with keyed opening 140. With the keyed column aligned with keyed opening 140, the plurality of actuation lines 128 and plug connectors 160 may be aligned with at least one barb connector 150 positioned within a corresponding actuation port 137. It should be appreciated that actuation lines 128 may have a minimum slack prior to assembly to facilitate a connection between plug connectors 160 and barb connectors 150. As described further below, upon connecting plug connectors 160 to barb connectors 150, actuation lines 128 may be tensioned by a biasing mechanism disposed about the plurality of cables 141.

In the example, distal ends 156 may be press-fit into actuation ports 137 and positioned against stop walls 137A, thereby securing barb connectors 150 to a fixed position relative to second portion 130 prior to assembly with first handle 110. At least a portion of body 152, such as proximal end 154, may be disposed within keyed opening 140 as distal ends 156 are received in actuation ports 137. It should be appreciated that the press-fit connection between distal ends 156 and actuation ports 137 may at least partially deform distal end 156 (e.g., via radial compression), such that barb connectors 150 may remain at the fixed position until extracted by plug connectors 160 (as described further herein).

As seen in FIG. 10, as distal end 114 is pushed distally toward proximal end 138, fluidics ports 135 may be received within fluidics ports 115. The pair of sealing mechanisms 146 on each fluidics port 135 may abut against an interior channel of fluidics ports 115, thereby forming a sealed, fluid connection with fluidics tubes 124 (FIG. 2) of first handle 110. It should be appreciated that, as fluidics ports 135 translate through fluidics ports 115 to a plurality of positions, second portion 130 may be configured to maintain the sealed connection at variable distances via the pair of sealing mechanisms 146. Stated differently, sealing mechanisms 146 may be configured to maintain a continuous seal as fluidics ports 135 are received in fluidics ports 115, irrespective of a relative position of proximal end 138 relative to distal end 114. In some embodiments, fluidics ports 115 may establish a fluid connection with fluidics ports 135 prior to actuation lines 128 becoming coupled with cables 141 via engagement of plug connectors 160 and barb connectors 150.

Figure 11:
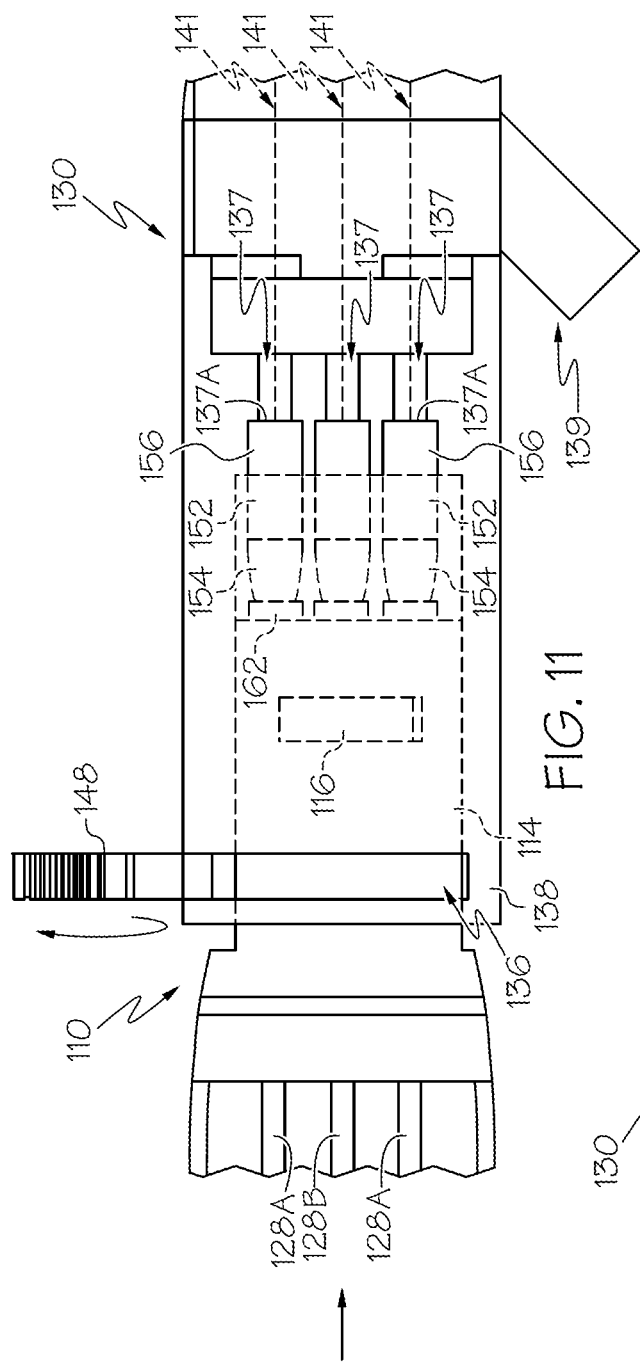
FIG. 11 is a partial side view of the reusable handle received within the disposable portion of the medical device of FIG. 1, with the first connectors of the reusable handle coupled to the second connectors of the disposable portion, according to aspects of this disclosure.

Referring now to FIG. 11, locking mechanism 148 may be actuated from the locked position (FIG. 9), with locking mechanism 148 received within slot 136, to an unlocked position where locking mechanism 148 is removed from slot 136. The plurality of plug connectors 160 may extend into second portion 130 and engage the plurality of barb connectors 150, thereby coupling actuation lines 128 (disposed within body 112) to the plurality of cables 141 disposed within body 132. Distal end 114 may be moved distally relative to proximal end 138 until first handle 110 experiences a hard stop, as defined by the interaction of plug connectors 160 with barb connectors 150. It should be appreciated that, with distal ends 156 abutting against stop walls 137A and press-fit into actuation ports 137, plug connectors 160 may be configured to apply a compressive force against proximal ends 154 until forming a snap-fit connection with body 152.

Figure 12:
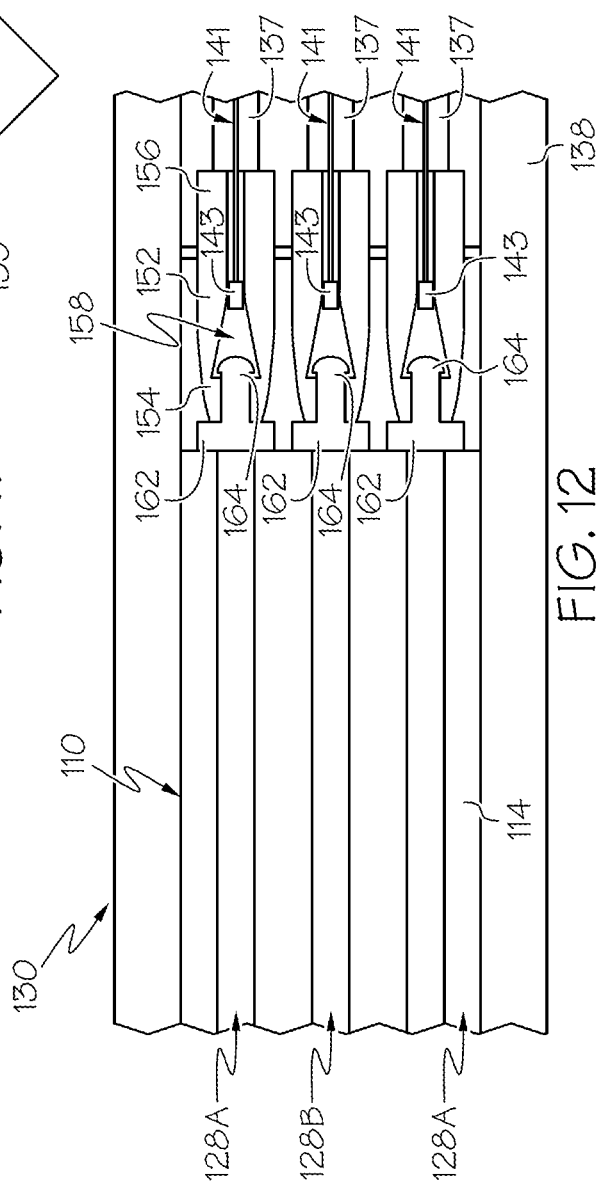
FIG. 12 is a partial cross-sectional view of the reusable handle received within the disposable portion of the medical device of FIG. 1, with the first connectors of the reusable handle coupled to the second connectors of the disposable portion, according to aspects of this disclosure.

For example, as seen in FIG. 12, distal tip 164 of each of the plurality of plug connectors 160 (enlarged relative to a proximally-adjacent portion of plug connector 160) may be urged through the proximal opening at proximal end 154 and received within a socket cavity 158 of body 152. Proximal base 162 may be disposed externally of socket cavity 158, and may engage proximal end 154 when arriving at the hard stop. Distal movement of barb connector 150 may be inhibited by the engagement of distal end 156 against stop wall 137A, such that plug connectors 160 may push against barb connectors 150 until distal tip 164 is received through proximal end 154. In some embodiments, first handle 110 and/or second portion 130 may be configured to generate a feedback (e.g., tactile, audible, etc.) when distal tip 164 is received within socket cavity 158. In some examples, distal tip 164 may have a proximal ledge that is configured to engage an interior, planar wall of socket cavity 158. In this instance, proximal retraction of plug connector 160 from barb connector 150 may be at least partially inhibited via the engagement between the proximal ledge and planar wall.

With the proximal ledge of distal tip 164 abutting against the planar wall of socket cavity 158, plug connector 160 may be securely coupled to barb connector 150 up to a predetermined force threshold (e.g., an amount of proximally-directed force on plug connector 160). In this instance, movement of the plurality of actuation lines 128 within first handle 110 (e.g., via knobs 123) may provide for movement of barb connectors 150 and cables 141 within second portion 130. As described further herein, first handle 110 may be configured to decouple plug connectors 160 from barb connectors 150 upon the application of a proximal, pulling force that is greater than the predetermined force threshold.

It should be appreciated that distal ends 156 may include a distal opening from which cables 141 may be received within body 152. In the embodiment, each of the plurality of cables 141 may be at least partially received within socket cavity 158 of a corresponding barb connector 150 through the distal opening. For example, cables 141 may include a proximal end 143 that is received within socket cavity 158, and proximal end 143 may have a relatively greater cross-sectional dimension than the distal opening of barb connector 150 at distal end 156. Accordingly, cables 141 may be fixed to barb connectors 150. By way of illustrative example, proximal end 143 may include a crimp, a knot, a protrusion, a flared end, etc. As described further below, each cable 141 may include a biasing mechanism that is configured to bias cables 141, and a corresponding actuation line 128 coupled thereto, via the intermediate connection between plug connectors 160 and barb connectors 160. The biasing mechanism may bias cables 141 in a distally-directed direction (e.g., toward distal tip 184) when medical device 100 is in an assembled state.

Figure 13:
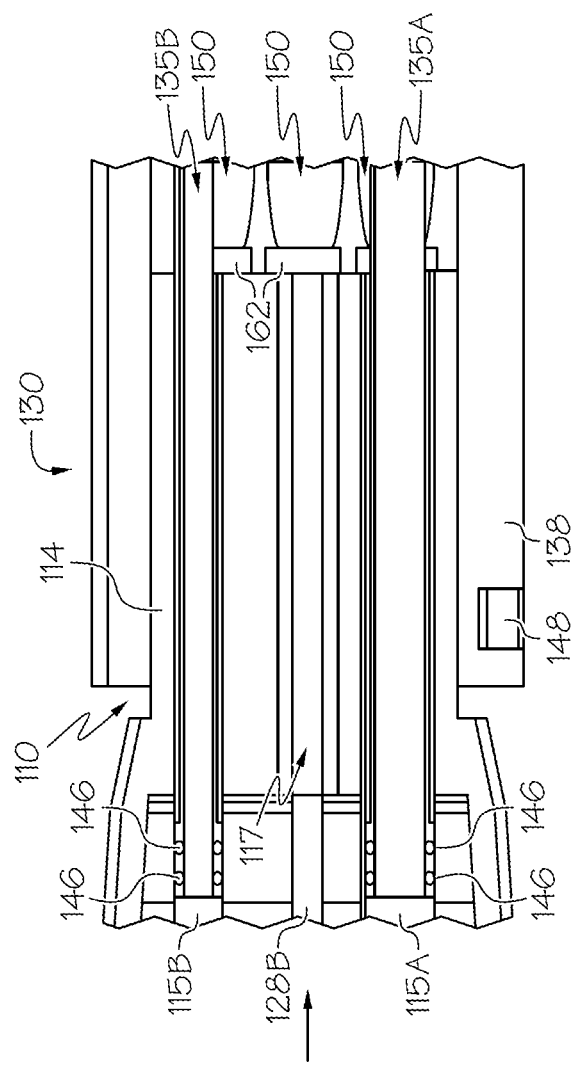
FIG. 13 is a partial cross-sectional view of the reusable handle received within the disposable portion of the medical device of FIG. 1, with the fluidics tubes of the disposable portion received within the fluidics ports of the reusable handle, according to aspects of this disclosure.
Figure 14:
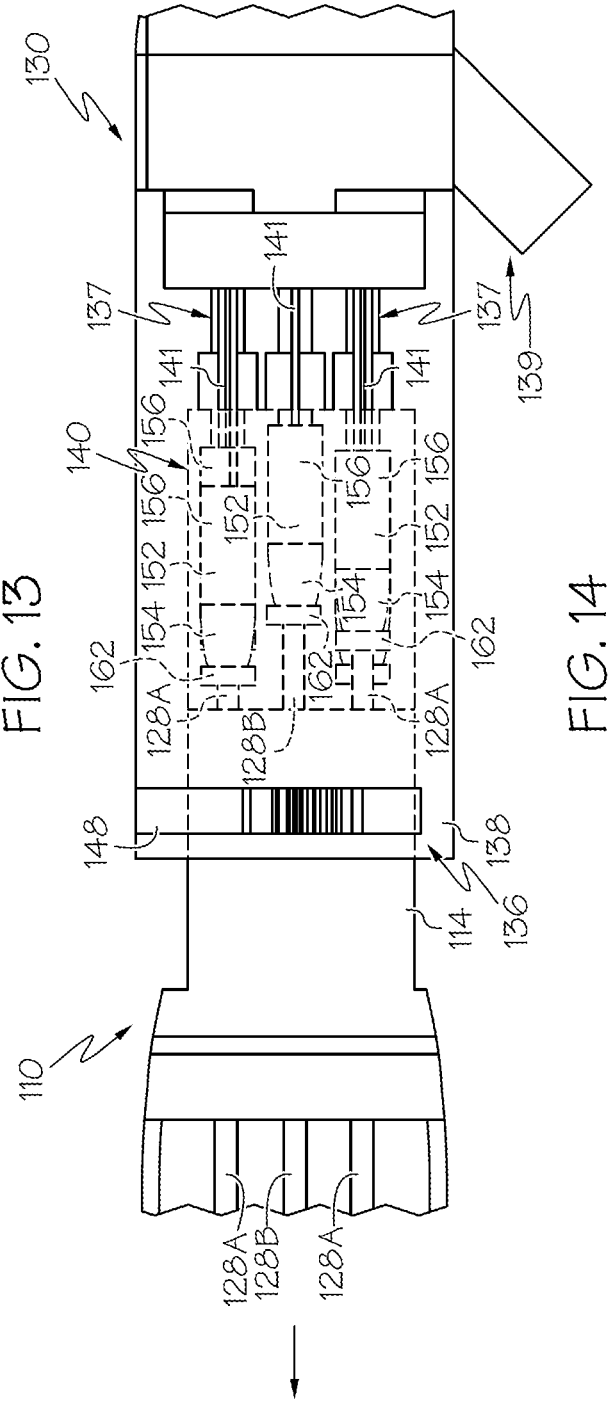
FIG. 14 is a partial side view of the reusable handle received in the disposable portion of the medical device of FIG. 1, with the first connectors of the reusable handle moving the second connectors relative to the disposable portion, according to aspects of this disclosure.

As seen in FIG. 13, with distal end 114 fully received within proximal end 138, fluidics ports 135 may be substantially disposed through fluidics ports 115. Sealing mechanisms 146 may maintain a sealed connection between first handle 110 and second portion 130 across a plurality of positions of fluidics ports 135 relative to fluidics ports 115 via sealing mechanisms 146. As seen in FIG. 14, distal end 114 may be retracted proximally relative to proximal end 138 to pull the plurality of plug connectors 160 proximally relative to keyed opening 140. With plug connectors 160 coupled to the plurality of barb connectors 150, first handle 110 may be configured to decouple barb connectors 160 from the plurality of actuation ports 137 upon application of a proximal-pulling force. In this instance, barb connectors 150 and cables 141 may move freely within keyed opening 140 (e.g., in response to actuation of knobs 123) during use of medical device 100 in a procedure. In some embodiments, cables 141 may be in a slacked configuration when barb connectors 150 remain positioned against stop walls 137A, such that a proximal retraction of barb connectors 150 from stop walls 137A may provide a longitudinal tension in cables 141 and actuation lines 128.

Locking mechanism 148 may be actuated from the unlocked position (FIG. 11) to the locked position to engage distal end 114. For example, locking mechanism 148 may be received in slot 136, and at least a portion of locking mechanism 148 may engage groove 116 to secure second portion 130 to first handle 110. Locking mechanism 148 may secure first handle 110 to second portion 130 at a fixed, axial length during use of medical device 100 in a procedure. The plurality of actuation lines 128 may be configured to move relative to first handle 110 and second portion 130 while locking mechanism 148 is in the locked position. In some embodiments, locking mechanism 148 may become elastically deformed when engaging groove 116, thereby increasing a connection strength between first handle 110 and second portion 130. Deformation of locking mechanism 148 may be further configured to inhibit subsequent use of second portion 130 after completion of the procedure.

Figure 15:
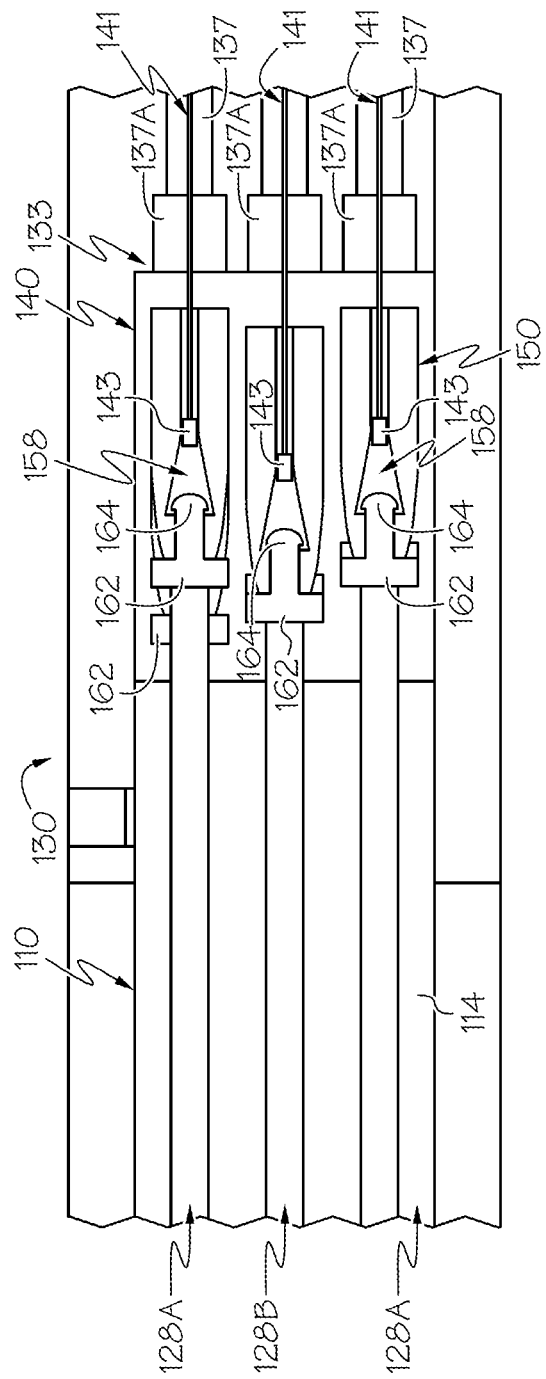
FIG. 15 is a partial cross-sectional view of the reusable handle received in the disposable portion of the medical device of FIG. 1, with the first connectors received within the second connectors of the disposable portion, according to aspects of this disclosure.

Referring now to FIG. 15, first handle 110 may be configured to actuate distal end 184 via the one or more knobs 123 due to the plurality of actuation wires 128 being movably coupled to the plurality of cables 141 via the engagement of plug connectors 160 and barb connectors 150. For instance, the actuation of knobs 123 may provide for a translation of one or more actuation wires 128, plug connectors 160, and the corresponding cables 141 coupled thereto via barb connectors 150. Translating cables 141 may provide for a movement of distal end 184 and/or distal tip 186, such as, for example, articulating, bending, deflecting, pivoting, and/or moving distal end 184 relative to proximal end 188.

Figure 16:
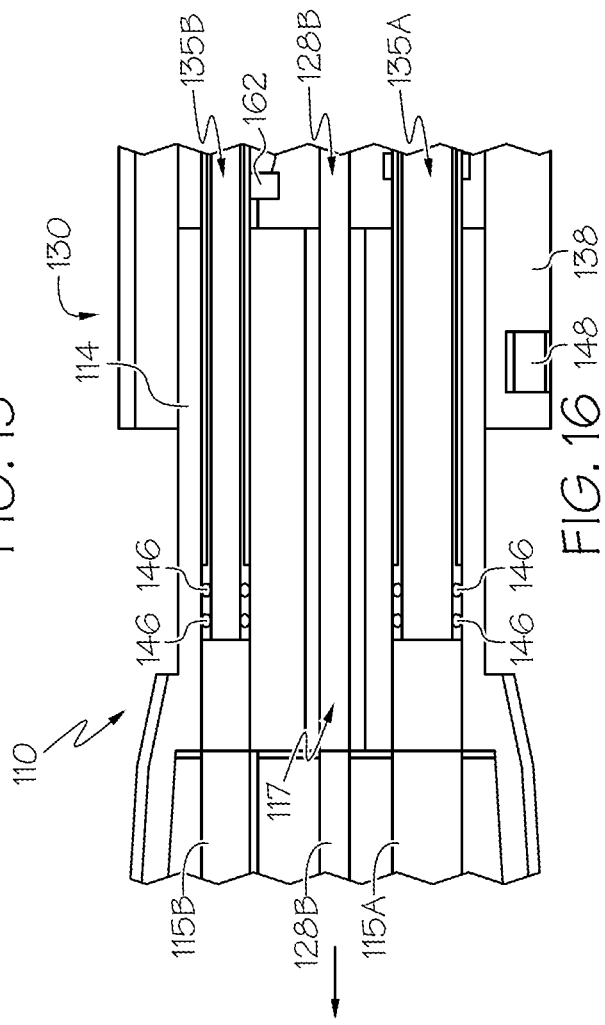
FIG. 16 is a partial cross-sectional view of the reusable handle received in the disposable portion of the medical device of FIG. 1, with the fluidics tubes of the disposable portion received within the fluidics ports of the reusable handle, according to aspects of this disclosure.

A range of longitudinal motion of the plurality of actuation lines 128 and cables 141 may be defined by keyed opening 140, and particularly a pocket formed between a distally-facing surface of distal end 114 and a proximally-facing surface of proximal end 138. In other words, keyed opening 140 may provide a space between first handle 110 and second portion 130 for barb connectors 150 to translate during use of medical device 100, such as, for example, in response to a movement of actuation wires 128. It should be appreciated that, upon removal of barb connectors 150 from the press-fit connection with actuation ports 137, distal ends 156 may return to a default size and/or shape that is relatively greater than a profile of actuation ports 137. Accordingly, barb connectors 150 may be inhibited from returning into actuation ports 137 upon proximal retraction of distal ends 156 from stop walls 137A, thereby inhibiting subsequent use of medical device 100 after completion of a procedure. As seen in FIG. 16, the plurality of fluidics ports 135 may maintain a fluid seal within fluidics ports 115, via sealing mechanisms 146, when first handle 110 becomes locked at the fixed position relative to second portion 130.

Figure 17:
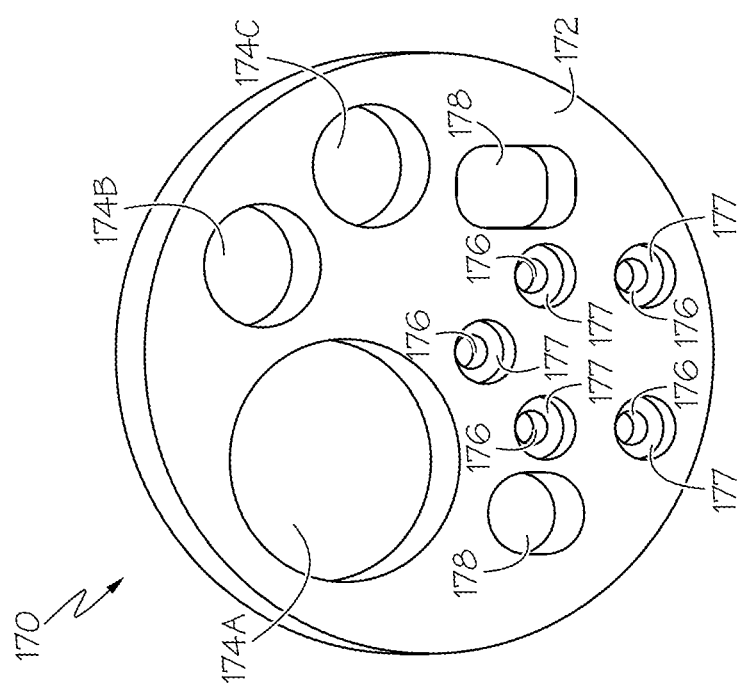
FIG. 17 is a perspective view of a compression plate of the medical device of FIG. 1, according to aspects of this disclosure.

Referring now to FIG. 17, second portion 130 may include a compression plate 170 having a body 172 with one or more openings. For example, compression plate 170 may include a first fluidics opening 174A, a second fluidics opening 174B, and a third fluidics opening 174C (collectively referred to herein as "fluidics openings 174") extending through body 172. Each of the fluidics opening 174 may be aligned with, and sized to receive, a fluidics channel (not shown) extending through second portion 130, and distally from fluidics ports 135. Compression plate 170 may further include a plurality of actuation openings 176, each of which may include a stop wall 177. The plurality of actuation openings 176 may be sized and configured to receive the plurality of cables 141 extending through second portion 130, and distally from the plurality of barb connectors 150.

In the embodiment, each of the plurality of cables 141 may be a Bowden cable, which includes a coil/spring surrounding the cable. The spring acts as a biasing mechanism and extends between compression plate 170 and a terminal end of cable 141 at distal tip 186. The spring may be configured to tension cable 141 during assembly and use of medical device 100 by increasing a rigidity of cables 141. In the example, the spring may be disposed about an exterior surface of cable 141, and may extend along at least a portion of a longitudinal length of cable 141. With actuation lines 128 coupled to cables 141 via the connection between plug connectors 160 and barb connectors 150, the spring may further tension actuation lines 128 during use of medical device 100. In some examples, the spring may provide a guide and/or channel for cables 141 to pass through between compression plate 170 and distal tip 186, and may increase a torsional strength of cables 141.

Still referring to FIG. 17, stop walls 177 may have a diameter that is sized relatively smaller than a cross-sectional dimension of the spring disposed about each cable 141. Accordingly, the spring may engage stop wall 177, and may be inhibited from extending proximally through actuation openings 176. The spring may be compressed against stop wall 177, thereby generating a tensile force on cable 141. Compression plate 170 may further include one or more electronic cable openings 178 for receiving one or more electronic cables extending through electronic cable ports 111 (FIG. 5) and electronic cable ports 131 (FIG. 7).

Figure 18:
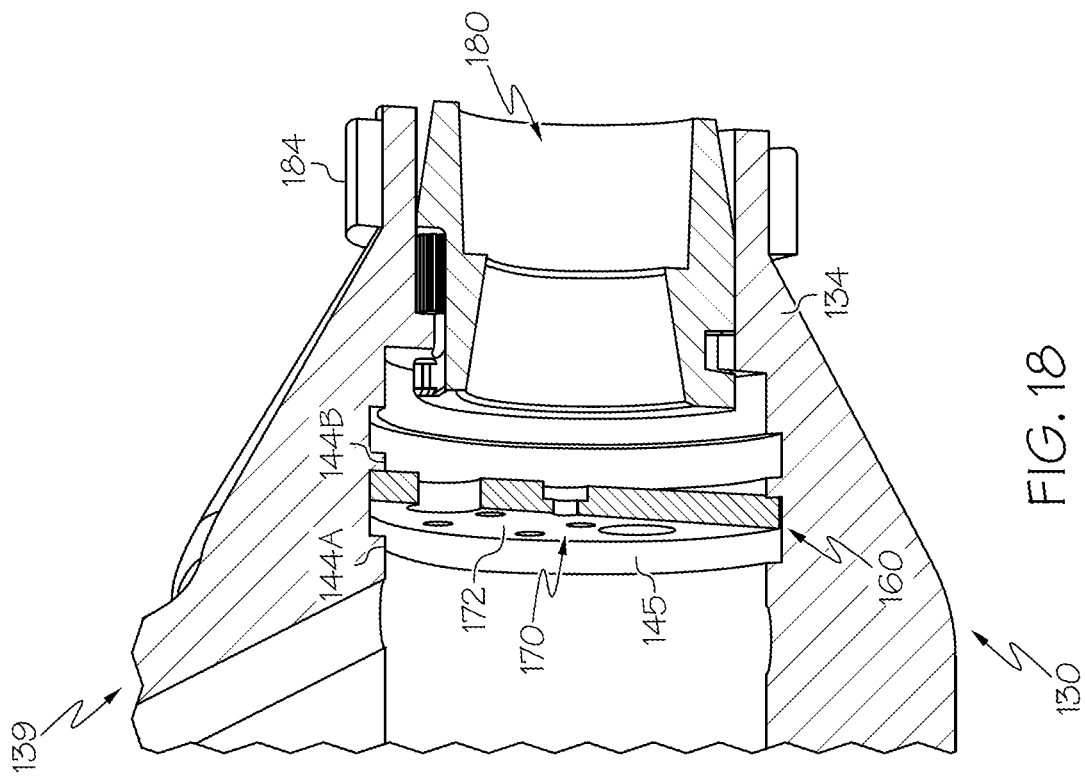
FIG. 18 is a partial cross-sectional view of the compression plate of FIG. 17 disposed within the disposable portion of the medical device of FIG. 1, according to aspects of this disclosure.

Referring now to FIG. 18, compression plate 170 may be disposed within second portion 130 in a cavity 145 positioned adjacent to distal end 134. Cavity 145 may be defined between a first internal ledge 144A and a second internal ledge 144B. Cavity 145 may be sized and shaped to receive compression plate 170 and a second biasing mechanism (not shown) disposed between the pair of internal ledges 144A, 144B. The second biasing mechanism may include a spring (e.g., a wave disk spring) that is configured to compress compression plate 170 against at least one of the pair of internal ledges 144A, 144B. In some examples, the second biasing mechanism may be positioned between first internal ledge 144A and compression plate 170 may be positioned against second internal ledge 144B, such that the second biasing mechanism may be operable to maintain compression plate 170 in a fixed position within cavity 145 by applying a distally-directed, compressive force against body 172.

During a procedure, it should be appreciated that first handle 110 may be positioned external to the subject, and at least a portion of second portion 130, such as tube assembly 180, may be received within the subject. Additionally, one or more materials (e.g., biological matter, solid particulates, fluid, etc.) from a target treatment site within the subject may be received (e.g., via suction) through tube assembly 180, second portion 130 (e.g., via first fluidics port 135A), and first handle 110 (e.g., via first fluidics port 115A and first fluidics tube 124A) for delivery to umbilicus assembly 190. Further, second fluidics tube 124B and third fluidics tube 124C may deliver water and/or pressurized air, respectively, to the target treatment site during the procedure. Distal tip 184 may be actuated (e.g., articulated) in response to an actuation of knobs 123 (FIG. 1), thereby causing one or more of the plurality of first actuation lines 128A to move a corresponding cable 141 that is attached to distal tip 184. A tool (e.g., an elevator) at distal tip 184 may be actuated (e.g., pivoted) in response to an actuation of at least one knob 123, thereby causing second actuation line 128B to move a corresponding cable 141 that is attached to the tool.

Referring to FIG. 19, upon completion of the procedure with medical device 100, a user may disassemble first handle 110 from second portion 130 by actuating locking mechanism 148 from the locked position to the unlocked position. In response to moving locking mechanism 148 outwardly from slot 136, first handle 110 may be pulled proximally to retract distal end 114 from within proximal end 138. As distal end 114 is moved outward from proximal end 138, the plurality of barb connectors 150 may be pulled proximally due to the continued engagement with the plurality of actuation lines 128 via plug connectors 160. In the example, barb connectors 150 may be pulled proximally until cables 141 are extended to a proximal extent (e.g., a proximalmost position), thereby inhibiting further movement of barb connectors 150 relative to second portion 130.

With distal tip 164 received within socket cavity 158, plug connector 160 may be securely coupled to barb connector 150 up to the predetermined force threshold. First handle 110 may be configured to decouple plug connectors 160 from barb connectors 150 upon the application of a proximal, pulling force that is greater than the predetermined force threshold. In the embodiment, with plug connectors 160 being rigid and barb connectors 150 being relatively more flexible and formed of a relatively softer material, plug connectors 160 may be configured to physically deform barb connectors 150 upon the application of force exceeding the predetermined force threshold.

In some examples, each of the plurality of barb connectors 150 may be configured such that body 152 may sustain an application of force up to a maximum force tolerance prior to experiencing deformation. The maximum force tolerance may range from about 30 pounds (lbs) to about 50 lbs, and particularly about 40 lbs. In the example, with second portion 130 including five barb connectors 150, the predetermined force threshold (e.g., a cumulative of the maximum force tolerance of each body 152) may range from about 150 lbs to about 250 lbs, and particularly about 200 lbs. It should be appreciated that the maximum force tolerance and predetermined force threshold may be greater than any tensile force endured by actuation wires 128 and/or cables 141 during routine use of medical device 100 in a procedure, thereby inhibiting premature disconnection. The maximum force tolerance and predetermined force threshold may be selectively adjusted based on a material composition, a geometry, and/or a position of one or more of plug connectors 160 and/or barb connectors 150.

Referring to FIG. 20, upon the application of the proximal, pulling force onto first handle 110 that exceeds about 200 lbs of total force, the plurality of barb connectors 150 may elastically deform, thereby allowing plug connectors 160 to be released from within socket cavity 158. For example, the opening at proximal ends 154 may expand upon the application of force, thereby increasing the size and/or shape of the proximal opening at proximal end 154, allowing distal tip 164 to exit therethrough. By way of further example, body 152 may tear open between proximal end 154 and distal end 156, thereby permitting removal of distal tip 164 from within body 152 at the tear site. It should be appreciated that barb connectors 150 may be deformed in various other suitable manners than those shown and described herein without departing from a scope of this disclosure. In other embodiments, first handle 110 may include one or more actuators (e.g., buttons, levers, knobs 123) for generating the proximal force to separate plug connectors 160 from barb connectors 150.

Medical device 100 may be configured to inhibit subsequent use of second portion 130 via a deformation of the plurality of barb connectors 150. Accordingly, with second portion 130 and tube assembly 180 decoupled from first handle 110, second portion 130 and tube assembly 180 may be disposed of by a user of medical device 100. First handle 110 may be reprocessed and cleaned for further use by accessing the plurality of fluidics tubes 124 via fluidics ports 115 at distal end 115. As described in detail above, fluidics tubes 124 may have a relatively short length, and may be rigid, to further facilitate cleaning first handle 110 with various cleaning instruments (e.g., a brush).

It should be appreciated that umbilicus assembly 190 may be selectively coupled to first handle 110 in a similar manner as that described and shown above with respect to second portion 130 and first handle 110. In this instance, an interface between port 119 and distal umbilicus connector 191 may include one or more components that are similar to those of first handle 110 and second portion 130 between distal end 114 and proximal end 138, respectively. In some embodiments, umbilicus assembly 190 may be decoupled from first handle 110 in a manner that inhibits further use of umbilicus assembly 190 (e.g., by altering one or more fluid and/or electronic cable connections). With second portion 130, tube assembly 180, and umbilicus assembly 190 decoupled from first handle 110 and discarded, medical device 100 may minimize cross-contamination between subjects and/or across multiple procedures. Further, by reutilizing first handle 110 in further procedures, medical device 100 may minimize a material waste by limiting the number of components discarded after each procedure.

In other embodiments, first handle 110 may be configured and operable to couple with various other components having a similar connection interface (e.g., proximal end 138, keyed opening 140, barb connectors 150, and more) as that of second portion 130 shown and described above.

FIG. 21 shows an exemplary medical device 200 in accordance with another example of this disclosure. Except as otherwise described herein, medical device 200 may be configured and operable similar to medical device 100 shown and described above. Accordingly, like reference numerals are used to identify like components.

Medical device 200 may include a first handle 210 and a second portion 230 that may be similar to first handle 110 and second portion 130, respectively. First handle 210 may include a body 212 having a distal end 214 with the plurality of actuation lines 128 (e.g., first actuation lines 128A and/or second actuation lines 128B) extending therethrough. Each of the plurality of actuation lines 128 may include an extension line 228 extending distally from a distal end of actuation lines 128, and secured to the distal end by various suitable connections (e.g., welding, crimping, rivets, pinning, etc.). For example, extension lines 228 may be at least partially received within a slot at the distal end of actuation lines 128. In the embodiment, extension lines 228 may have a flat and/or planar profile relative to a circular and/or cylindrical shape of actuation lines 128. In some embodiments, extension lines 228 may be formed of a rigid material, such as, for example, stainless steel, and may be rigid. As described in further detail herein, each of the plurality of extension lines 228 may extend through second portion 230 when first handle 210 is coupled thereto.

First handle 210 may include a distal flange or ledge 216 extending about a circumference of body 212 at distal end 214. Distal ledge 216 may have one or more openings (see FIG. 25) sized to receive one or more components of second portion 230 to thereby couple second portion 230 to first handle 210. Second portion 230 may include a body 232 having a longitudinal length defined between a distal end 233 and a proximal end 234. Distal end 233 may be configured to receive proximal end 184 of tube assembly 180, and proximal end 234 may be configured to at least partially receive distal end 214 of first handle 210. Although not shown, it should be appreciated that first handle 210 and second portion 230 may include one or more fluidics tubes and/or ports extending through body 212 and body 232, respectively. The fluidics tube(s) of first handle 210 may be substantially similar to fluidics tubes 124, and the fluidics port(s) of second portion 230 may be substantially similar to fluidics ports 115.

Still referring to FIG. 21, second portion 230 may include a plurality of frictional connectors 260 disposed within an opening in body 232 at proximal end 234. It should be appreciated that the opening at proximal end 234 may be substantially similar to keyed opening 140 shown and described above. Second portion 230 may include at least one frictional connector 260 and cable 141 for each of the plurality of actuation lines 128 in first handle 210. Each of the plurality of frictional connectors 260 may include a distal leg 270 extending distally from frictional connector 260, and the plurality of frictional connectors 260 may be coupled (e.g., crimped) to the plurality of cables 141 along distal leg 270. Distal leg 270 may include a protrusion, a tab, a pin, and/or other member that extends outwardly from an exterior of frictional connector 260, and that has a longitudinal length. The plurality of cables 141 may extend distally from the opening at proximal end 234 via one or more actuation ports 137.

Medical device 200 may further include a locking ring 240 movably coupled to an exterior surface of body 232 along proximal end 234. In the example, locking ring 240 may be disposed about an outer circumference of proximal end 234. Locking ring 240 may include a body 242 having a plurality of fastening mechanisms 244 extending proximally from body 242 for engaging first handle 210. For example, fastening mechanisms 244 may be configured to engage distal ledge 216 in response to the one or more openings of distal ledge 216 receiving fastening mechanisms 244 therethrough. The plurality of fastening mechanisms 244 may be positioned about a perimeter of body 242 in a first annular array. In some embodiments, fastening mechanisms 244 may include a hook, a clip, a clasp, and/or various other suitable devices capable of forming a mechanical connection with distal ledge 216. Locking ring 240 may further include a plurality of flange connectors 250 configured to slidably receive extension lines 228 when first handle 210 is received in second portion 230.

As best seen in FIG. 22, body 242 of locking ring 240 may have a circular shape extending about a center opening, and may include a central floor 246 disposed within the center opening defined by body 242. Locking ring 240 may include the plurality of flange connectors 250 positioned along central floor 246, with each flange connector 250 including a slot 252 disposed through central floor 246 for receiving at least one extension line 228. As described in further detail herein, each of the flange connectors 250 may be configured to receive at least one frictional connector 260 thereon, with distal leg 270 of each frictional connector 260 extending through slot 252 of each flange connector 250.

Locking ring 240 may further include a plurality of openings extending through central floor 246. For example, locking ring 240 may include a fluidics opening 247, a cable opening 248, and a plurality of perimeter openings 249. Fluidics opening 247 may be sized, shaped, and configured to receive one or more fluidics ports (not shown) from second portion 230 and through central floor 246. Cable opening 248 may be sized, shaped, and configured to receive one or more electrical cables (not shown) from first handle 210 and through central floor 246. The plurality of perimeter openings 249 may be configured to slidably receive at least a portion of body 232 (see FIGS. 24 and 26A-26B) to slidably couple locking ring 240 to second portion 230. Although not shown, it should be appreciated that frictional connectors 260 may be disposed over a top surface of flange connectors 250, such that frictional connectors 260 may be seated along central floor 246.

As further seen in FIG. 23, each of the plurality of flange connectors 250 may further include an arm 254 extending distally from a bottom surface of flange connector 250. Arms 254 may be positioned adjacent to slots 252 and, as described further below, may be configured to engage one or more components of second portion 230 during use of medical device 200 in a procedure. Although not shown, it should be appreciated that distal legs 270 may extend through slots 252 and be positioned adjacent to arms 254.

Figure 24:
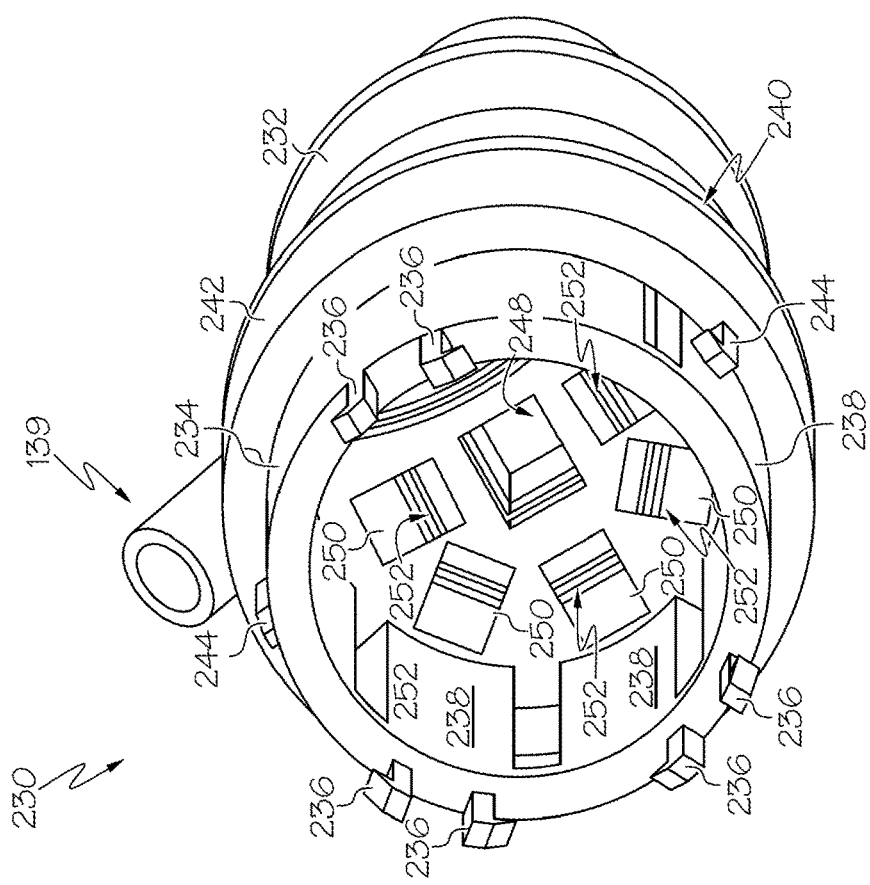
FIG. 24 is a perspective view of the locking ring of FIG. 22 coupled to the disposable portion of the medical device of FIG. 21, according to aspects of this disclosure.

Referring now to FIG. 24, locking ring 240 may be configured to receive at least one leg 238 of body 232 through each of the plurality of perimeter openings 249, thereby coupling body 242 to proximal end 234. Stated differently, proximal end 234 may be defined by a plurality of legs 238 extending distally from body 232. Locking ring 240 may be configured to move (e.g., translate) relative to body 232, and particularly slide along the plurality of legs 238 at proximal end 234. Second portion 230 may include a plurality of fastening mechanisms 236 extending proximally from proximal end 234. Fastening mechanism 236 may be configured to engage distal ledge 216 in response to the one or more openings of distal ledge 216 receiving fastening mechanisms 236. The plurality of fastening mechanisms 236 may be positioned about a perimeter of proximal end 234 in a second annular array that is different than the first annular array of fastening mechanisms 244 on locking ring 240. In some embodiments, fastening mechanisms 236 may include a hook, a clip, a clasp, and/or various other suitable devices capable of forming a mechanical connection with distal ledge 216.

Figure 25:
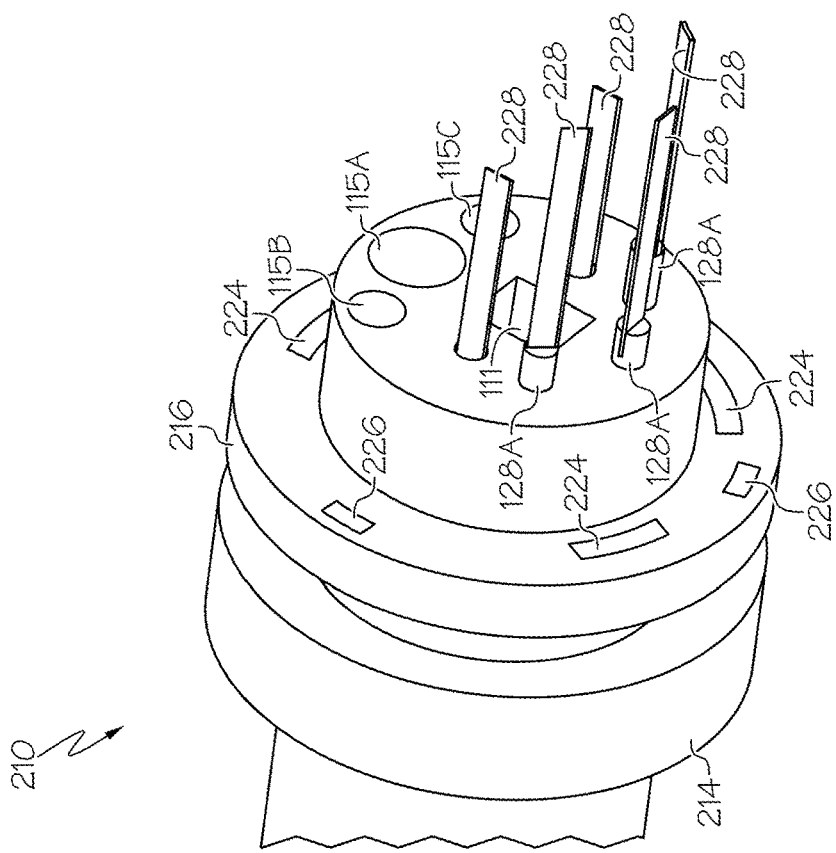
FIG. 25 is a partial perspective view of the reusable handle of the medical device of FIG. 21 including first connectors, according to aspects of this disclosure.

As seen in FIG. 25, distal ledge 216 may include one or more first openings 224 and one or more second openings 226, with first openings 224 sized to receive fastening mechanisms 236 of second portion 230 and second openings 226 sized to receive fastening mechanisms 244 of locking ring 240. In the example, first openings 224 may be sized and shaped to receive a pair of adjacent fastening mechanisms 236, and second openings 226 may be sized and shaped to receive a single fastening mechanism 244. As described in further detail herein, fastening mechanisms 236, 244 may be flexibly movable in response to receiving a radial force applied thereto.

The plurality of first openings 224 may be disposed about a perimeter of distal ledge 216 in a first pattern that corresponds to a relative position (e.g., the second annular array) of fastening mechanisms 236 about proximal end 234. The plurality of second openings 226 may be disposed about the perimeter of distal ledge 216 in a second pattern that corresponds to a relative position (e.g., the first annular array) of fastening mechanisms 244 about body 242. In some embodiments, the second annular array of fastening mechanisms 236, and the corresponding first pattern of the plurality of first openings 224, may be asymmetrical relative to body 232 and/or body 212, respectively. Accordingly, first handle 210 and second portion 230 may be collectively configured to facilitate an alignment of first handle 210 and second portion 230 when assembling medical device 200. In other words, second portion 230 may inhibit receipt of first handle 210 when first handle 210 is oriented relative to second portion 230 such that first openings 224 are misaligned with fastening mechanism 236.

Referring now to FIGS. 26A-26B, and according to an exemplary method of using medical device 200, first handle 210 may be coupled to second portion 230 in response to proximal end 234 receiving distal end 214. The plurality of fastening mechanisms 236 may extend through distal ledge 216 via the plurality of first openings 224. For example, each pair of fastening mechanisms 236 may at least partially flex (e.g., radially inward) toward one another when being received through first openings 224 until extending proximally outward from first openings 224. In this instance, fastening mechanisms 236 may flex (e.g., radially outward) away from another and engage a proximal surface of distal ledge 216, thereby securely attaching second portion 230 to first handle 210. In this instance, second portion 230 may be positioned at a fixed, axial length relative to first handle 210 during the procedure.

As seen in FIG. 27A, with first handle 210 oriented relative to second portion 230 to receive fastening mechanisms 236 through first openings 224, extension lines 228 may align with the plurality of frictional connectors 260 disposed within proximal end 234. In the example, frictional connectors 260 may be positioned over the plurality of flange connectors 250 prior to second portion 230 receiving first handle 210. The plurality of frictional connectors 260 may be coupled to the plurality of flange connectors 250, such as, for example, by partially extending through slots 252. The plurality of frictional connectors 260 may be positioned proximally relative to body 242. As described further herein, frictional connectors 260 may be configured to move distally relative to body 242 in response to locking ring 240 moving proximally relative to second portion 230.

Referring now to FIG. 27B, upon receipt of distal end 214 into proximal end 234, the plurality of extension lines 228 may be received through the plurality of frictional connectors 260. In some embodiments, a distal portion of extension lines 228 may be received through a proximal opening 272 of frictional connectors 260 (see FIGS. 28A-28B). As described in further detail herein, moving locking ring 240 proximally relative to proximal end 234 (see FIG. 27C) may cause the plurality of frictional connectors 260 to disengage body 242 due to the plurality of frictional connectors 260 being coupled to cables 141. In other words, frictional connectors 260 are maintained in a substantially fixed position relative to locking ring 240 via the connection with cables 141 in second portion 230, such that movement of locking ring 240 away from (e.g., proximal) second portion 230 and toward first handle 210 may cause frictional connectors 260 to pass through body 242.

Locking ring 240 may be positioned at a distal position relative to second body 230, such that the plurality of fastening mechanisms 244 may be separated from the distal ledge 216 by an axial distance. In this instance, locking ring 240 may be moved proximally relative to second portion 230, and toward first handle 210, from the distal position to a proximal position. In this instance, the plurality of frictional connectors 260 positioned against the plurality of flange connectors 250 may be urged through frictional connectors 250. As described in detail herein, each frictional connector 260 may be coupled to at least one cable 141, and each cable 141 may apply a (distally-directed) tensile force against frictional connectors 260 upon proximal movement of locking ring 240. Accordingly, with frictional connectors 260 connected to cables 141, frictional connectors 260 may be pulled through flange connectors 250 as locking ring 240 moves proximally toward handle 210 and away from cables 141. In some embodiments, frictional connectors 260 may not be in tension until locking ring 240 moves relative to cables 141 (FIG. 27C).

As seen in FIG. 28A, each of the plurality of frictional connectors 260 may include a housing 262 defined by a proximal end 264 and a distal end 266. Proximal end 264 may include proximal opening 272, and distal end 266 may include a distal opening 274, each of which may be sized and shaped to receive extension line 228 therethrough. Housing 262 may include at least a first wall 261 and at least a second wall defined by a narrowed portion 263 and an expanded portion 268. Housing 262 may further include a cavity 269 defined between first wall 261, narrowed portion 263, and expanded portion 268. It should be appreciated that a size of cavity 269 may be greater between first wall 261 and expanded portion 268 relative to first wall 261 and narrowed portion 263. In other words, a radial distance between first wall 261 and narrowed portion 263 may be less than a radial distance between first wall 261 and expanded portion 268.

In the example, housing 262 may include a movable ball 265 (e.g., a ball bearing) disposed within cavity 269. Movable ball 265 may be rigid and formed of a rigid material, such as, for example, a metal, metal alloy, stainless steel, and more. As described in further detail below, movable ball 265 may be configured to move within cavity 269, and engage extension line 228 to lock extension line 228 within housing 262. Frictional connector 260 may include a unidirectional friction device configured to allow extension line 228 to move freely through cavity 269 in a single (e.g., distal) direction, and to generate a frictional resistance against relative movement of extension line 228 in an opposite (e.g., proximal) direction.

Still referring to FIG. 28A, with movable ball 265 positioned adjacent to expanded portion 268, extension line 228 may be received through the opening at proximal end 264, translate through cavity 269, and extend distally from housing 262 via the opening at distal end 226 without constraint. It should be appreciated that movable ball 265 may move freely within housing 262 when positioned adjacent to expanded portion 268 due to the increased space in cavity 269 at expanded portion 268 relative to a corresponding space in cavity 269 at narrowed portion 263.

Referring now to FIG. 28B, movable ball 265 may be moved relative to cavity 269 in response to a movement of extension line 228 and/or housing 262 relative to one another. For example, housing 262 may pull movable ball 265, from a portion of cavity 269 adjacent to expanded portion 268 to a portion of cavity 269 adjacent to narrowed portion 263, when moving distally relative to extension line 228. Housing 262 of each of the plurality of frictional connectors 260 may be pulled distally by a (distally-directed) tensile force applied thereto by the plurality of cables 141 connected to each housing 262 via distal leg 270. Alternatively, distal movement of extension line 228 relative to housing 262 may move movable ball 265 toward narrowed portion 263. In this instance, narrowed portion 263 may exert a radial force onto movable ball 265, thereby allowing movable ball 265 to abut against extension line 228. Extension line 228 may be wedged between movable ball 265 and first wall 261, thereby fixing an axial position of frictional connector 260 and extension line 228 relative to one another. In this instance, frictional connector 260 may generate a frictional resistance between movable ball 265 and extension line 228 to securely fix an axial position of extension line 228 relative to housing 262. Accordingly, frictional connectors 260 may engage extension lines 228 (e.g., via movable ball 265), thereby tensioning the plurality of actuation lines 128 coupled to extension lines 228 as a result of the tensile force applied to frictional connectors 260 by cables 141.

As seen in FIG. 27C, locking ring 240 may be positioned at the proximal position with fastening mechanisms 244 engaged to distal ledge 216. For example, each fastening mechanism 244 may at least partially flex (e.g., move radially) when being received through second openings 226 until extending proximally outward from second openings 226. In this instance, fastening mechanisms 244 may flex back to an original position and engage a proximal surface of distal ledge 216, thereby securely attaching locking ring 240 to first handle 210. In this instance, second portion 230 may be positioned at a fixed, axial length relative to first handle 210 during the procedure. Locking ring 240 may move relative to the plurality of frictional connectors 260 when translating from the distal position to the proximal position due to frictional connectors 260 being fixed to the plurality of extension lines 228. In some embodiments, frictional connectors 260 may be extended through flange connectors 250 via slots 252 when locking ring 240 is moved proximally relative to second portion 230. It should be appreciated that flange connectors 250 may be partially deformed and/or formed of a flexible material to facilitate passage of frictional connectors 260 through slots 252. In other embodiments, flange connector 250 may be spring-loaded and operable to expand when receiving frictional connector 260.

Accordingly, the plurality of frictional connectors 260 may be disengaged from the plurality of flange connectors 250, and positioned distally relative to body 242, when locking ring 240 is in the proximal position. As described above, each frictional connector 260 may be coupled (e.g., crimped) to a proximal end of at least one of the plurality of cables 141 via distal leg 270. Accordingly, each extension line 228 may be coupled to at least one cable 141 via the intermediate connection to frictional connector 260. Locking ring 240 may be configured to increase a tension in cables 141 as body 242 is moved from the distal position to the proximal position. In the example, flange connectors 250 may be configured to permit frictional connectors 260 to pass through slot 252 when a predefined tensile force is generated in extension lines 228 and/or cables 141.

In this instance, with extension lines 228 and cables 141 tensioned by locking ring 240, distal tip 184 (FIG. 1) may be actuated (e.g., articulated) in response to an actuation of knobs 123, thereby causing one or more of the plurality of actuation lines 128 to move a corresponding cable 141 that is attached together via frictional connector 260. A tool (e.g., elevator) at distal tip 184 may be actuated (e.g., pivoted) in response to an actuation of at least one knob 123, thereby causing second actuation line 128B to move a corresponding cable 141 that is attached to the tool.

Upon completion of the procedure with medical device 200, a user may disassemble first handle 210 and second portion 230 by initially transitioning the plurality of frictional connectors 260 from the locked configuration (see FIG. 28B) to the unlocked configuration (see FIG. 28A). In the example, as explained further below, locking ring 240 may be configured to move movable ball 265 within cavity 269 from against narrowed portion 263 (FIG. 28B) and to expanded portion 268 (FIG. 28A), to thereby unlock extension line 228. For example, upon disengaging the plurality of fastening mechanisms 244 from distal ledge 216, locking ring 240 may move distally along proximal end 234 until arms 254 engage the plurality of frictional connectors 260. Fastening mechanisms 244 may disengage distal ledge 216 in response to manually manipulating fastening mechanisms 244 (e.g., via a tool or by hand) such that fastening mechanisms 244 elastically deform and release distal ledge 216. In other examples, fastening mechanisms 244 may disengage distal ledge 216 in response to rotation of locking ring 240 in one or more directions.

As seen in FIG. 27D, arms 254 may be received through the opening of frictional connectors 260 (e.g., at proximal ends 264) to dislodge movable ball 265 from narrowed portion 263. In this instance, with movable ball 265 pushed distally within cavity 269 toward expanded portion 268 (see FIG. 28A), the frictional resistance between the plurality of frictional connectors 260 and extension lines 228 may be removed. Accordingly, extension lines 228 and housings 262 may move freely relative to one another. In this instance, the plurality of fastening mechanisms 236 may be disengaged from distal ledge 216, and first handle 210 may be removed from within second portion 230. Fastening mechanisms 236 may disengage distal ledge 216 in response to manually manipulating fastening mechanisms 236 (e.g., via a tool or by hand). With second portion 230 disconnected from first handle 210, a user of medical device 200 may discard second portion 230 and reprocess first handle 210 for subsequent uses.

Figure 29:
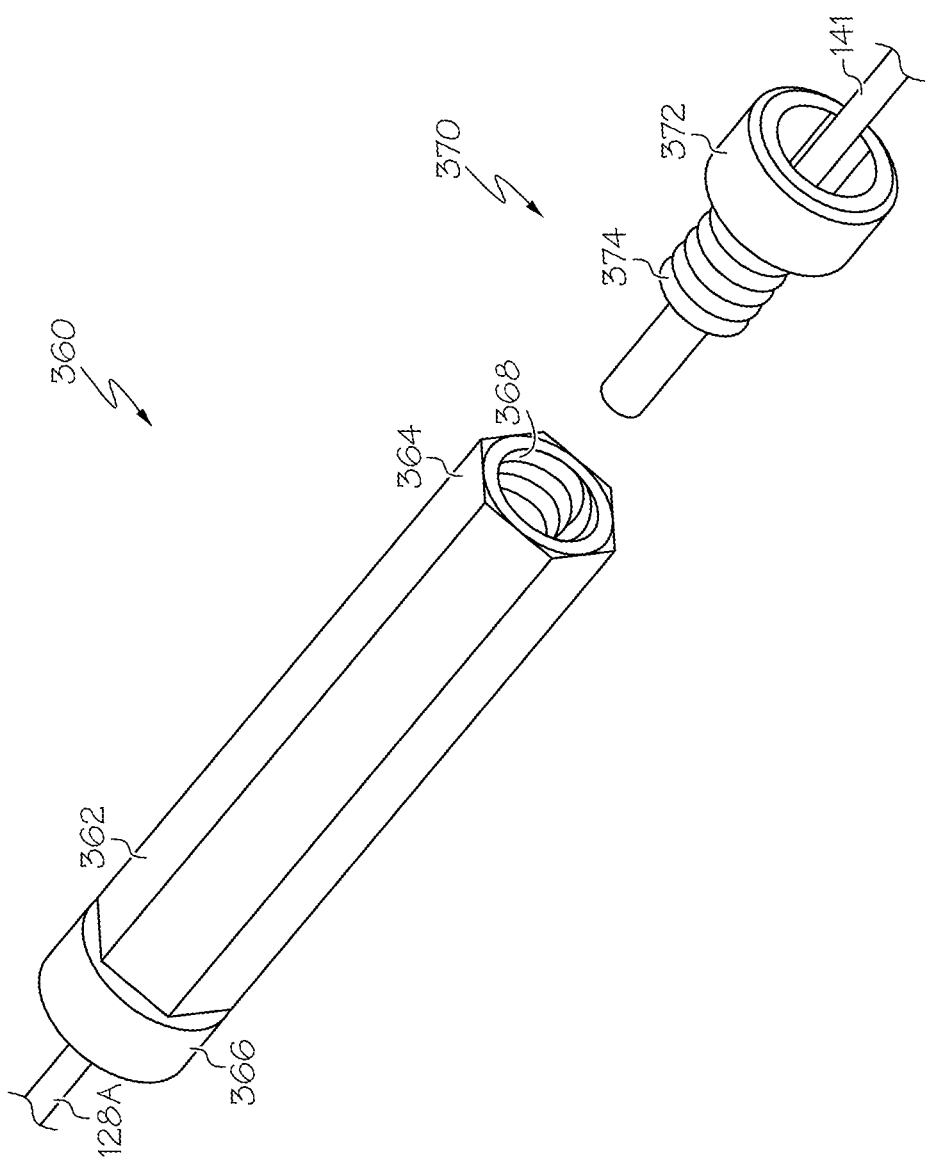
FIG. 29 is a partial perspective view of another exemplary connector mechanism, according to aspects of this disclosure.

FIG. 29 shows an exemplary connector 360 in accordance with another example of this disclosure. It should be understood that connector 360 may be readily incorporated into medical devices 100, 200 described above. It should further be understood that, in many respects, connector 360 functions similar to connectors 150, 160, 250, 260 shown and described above.

For example, connector 360 may include a nut end 362 and a bolt end 372 (e.g., a vented bolt). Nut end 362 may have a longitudinal length defined between a distal end 364 and a proximal end 366, with first actuation line 128A extending through and crimped inside nut end 362 at proximal end 366 thereby securely coupling a distal end of first actuation line 128A to connector 360. Nut end 362 may include a distal opening 368 at distal end 364, with an interior surface of nut end 362 having a threaded portion extending from distal opening 368 to proximal end 366. It should be appreciated that each of the plurality of actuation lines 128 may include at least one nut end 362 secured thereto.

Still referring to FIG. 29, bolt end 372 may include a proximal end 374 with an exterior surface having a threaded portion that is configured to mesh with the corresponding threaded portion of nut end 362. Bolt end 372 may be securely coupled (e.g., crimped) to a proximal end of cable 141, such that connector 360 may be configured to couple first actuation line 128A to cable 141 in response to nut end 362 receiving bolt end 372 through distal opening 368. It should be appreciated that each of the plurality of cables 141 may include at least one bolt end 372 secured thereto.

In exemplary use of connector 360 during a procedure, distal end 374 may be received through distal opening 368 such that the corresponding threaded portions of nut end 362 and bolt end 372 may mesh with one another. For example, at least one of nut end 362 and/or bolt end 372 may be rotated relative to the other, thereby coupling the pair of bolts 362, 372 to one another. In this instance, first actuation line 128A may be movably coupled to cable 141 via the intermediate connection via connector 360. It should be appreciated that first actuation line 128A may be tensioned by cable 141 via the connection by connector 360. Accordingly, actuation of one or more knobs 123 (see FIG. 1) may provide for a corresponding movement of cables 141 through extension lines 128.

Figure 30:
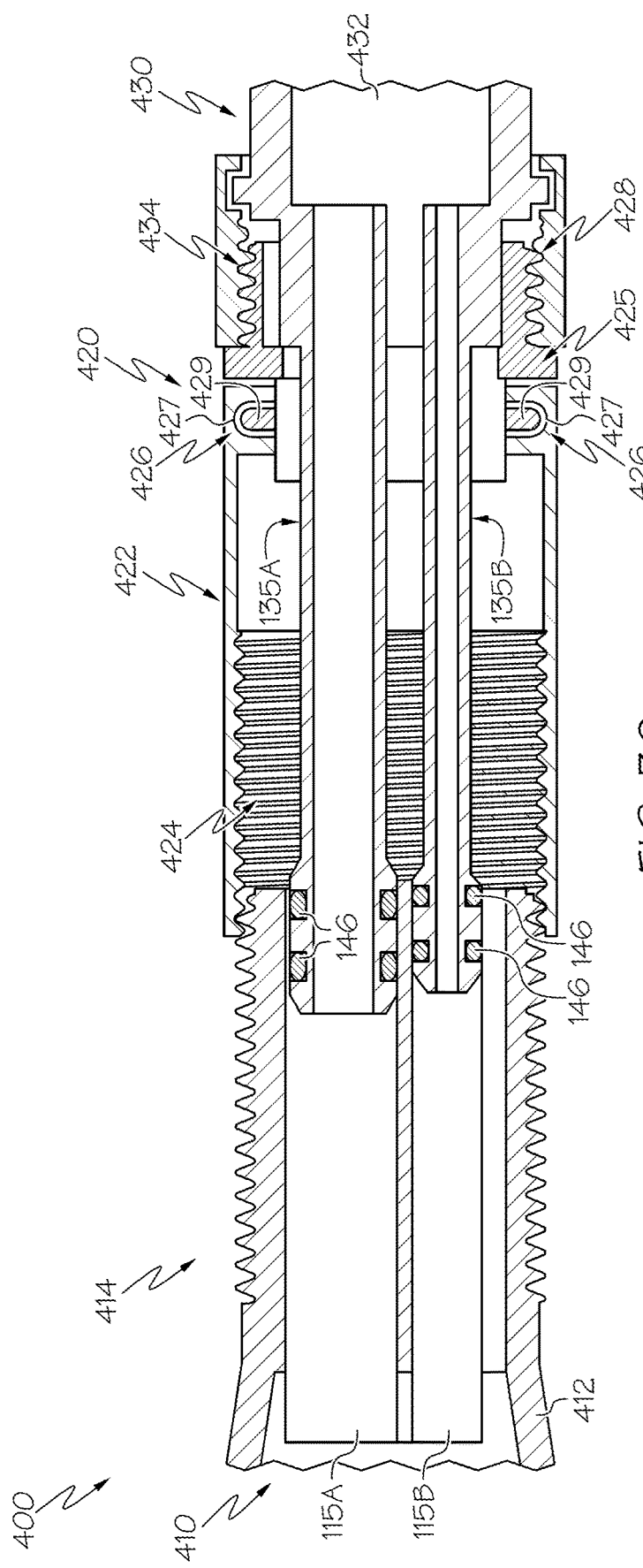
FIG. 30 is a partial cross-sectional view of another exemplary medical device including a reusable handle and a disposable portion coupled to one another with a keying mechanism, according to aspects of this disclosure.

FIG. 30 shows an exemplary medical device 400 in accordance with another example of this disclosure. Except as otherwise described herein, medical device 400 may be configured and operable similar to medical devices 100, 200 shown and described above. Accordingly, like reference numerals are used to identify like components.

For example, medical device 400 may include a first handle 410 and a second portion 430. First handle 410 may include a body with a distal end 412 that has an external threaded portion 414 disposed about an exterior surface of distal end 412. External threaded portion 414 may be positioned about an outer circumference of distal end 414. Second portion 430 may include a body with a proximal end 432 that has an internal threaded portion 434 disposed about an interior surface of proximal end 432. Internal threaded portion 434 may be positioned about an inner circumference of proximal end 432.

Still referring to FIG. 30, medical device 400 may further include a keying mechanism 420 configured to couple first handle 410 to second portion 430. Keying mechanism 420 may include a first body 422 having an internal threaded portion 424 disposed within an interior surface of first body 422. Internal threaded portion 424 may be configured to mesh with external threaded portion 414 when distal end 412 is received through a proximal opening of first body 422. Keying mechanism 420 may further include a second body 425 having an external threaded portion 428 disposed about an exterior surface of second body 425. External threaded portion 428 may be configured to mesh with internal threaded portion 434 when second body 425 is received through a proximal opening of second portion 430 at proximal end 432.

First body 422 may be coupled to second body 425 via a joint interface 426. For example, the joint interface 426 may include an aperture 427 formed about an exterior of first body 422, and a protrusion 429 extending radially outward from second body 425. Protrusion 429 of second body 425 may be received within aperture 427 of first body 422, thereby forming the joint interface 426. In the example, first body 422 and/or second body 425 may be configured to rotate relative to one another, and maintain a fixed axial position relative to one another, via the connection at joint interface 426. In this instance, protrusion 429 may move (e.g., rotate) through aperture 427 without causing an axial translation of first body 422 and/or second body 425 relative to one another. Accordingly, first body 422 and second body 425 may be configured to move in a first direction (e.g., rotate in a circumferential direction) relative to one another, and inhibited from moving in a second direction (e.g., translate in a proximal and/or distal direction) relative to one another.

In exemplary use of medical device 400, distal end 412 may be received through the proximal opening of first body 422, such that external threaded portion 414 may mesh with internal threaded portion 424. At least one of first handle 410 and/or first body 422 may be rotated relative to the other, thereby coupling first handle 410 to keying mechanism 420. Further, second body 425 may be received through the proximal opening of proximal end 432, such that external threaded portion 428 may mesh with internal threaded portion 434. At least one of second portion 430 and/or second body 425 may be rotated relative to the other, thereby coupling second portion 430 to keying mechanism 420. In this instance, fluid ports 115A, 115B may be fluidly coupled to fluidic ports 135A, 135B via the intermediate connection by keyed mechanism 420.

FIG. 31A-31B shows an exemplary first handle 510 and second portion 530 in accordance with another example of this disclosure. Except as otherwise described herein, first handle 510 and second portion 530 may be configured and operable similar to first handle 110 and second portion 130 shown and described above, respectively. Accordingly, like reference numerals are used to identify like components.

First handle 510 may include a body 512 with a distal end 514 that has a groove 516 disposed about an exterior surface of distal end 514. Groove 516 may be positioned about an outer circumference of distal end 514. In the example, groove 516 may include a recessed channel formed along the exterior surface of distal end 514. As described in further detail herein, groove 516 may be sized, shaped, and configured to receive at least a portion of second portion 530 to thereby couple first handle 510 to second portion 530.

Still referring to FIGS. 31A-31B, second portion 530 may include a body 532 with a proximal end 534 that has a flange 536 disposed about proximal end 534. In the example, body 532 may include a proximal opening 538 at proximal end 534, and flange 536 may be positioned about an outer edge of proximal opening 538. In some embodiments, flange 536 may be integral with body 532 and at least partially movable relative to proximal end 534, such that flange 536 may be configured to flex in response to receiving a radial force applied thereto. In some embodiments, flange 536 may include two or more segments that may be movable relative to one another. For example, flange 536 may include four segments having substantially similar cross-sectional profiles relative to one another. It should be appreciated that each of the segments of flange 536 may be independently movable relative to one another.

In exemplary use, second portion 530 may receive first handle 510 in response to the insertion of distal end 514 into proximal end 534. Flange 536 may be configured to flex radially outward relative to body 532 in response to second portion 530 receiving distal end 514 through proximal opening 538. First handle 510 may move distally through proximal opening 538 until groove 516 is aligned with flange 536. In this instance, flange 536 may flex radially inward relative to body 532 and into groove 516, thereby coupling first handle 510 to second portion 530. In this instance, flange 536 may form a snap connection with groove 516 that may inhibit movement (e.g., axial, rotative, etc.) of first handle 510 and second portion 530 relative to one another up to a predetermined force threshold for disassembling first handle 510 from second portion 530. In other embodiments, second portion 530 may include one or more pins (not shown) along proximal end 534 for receipt in groove 516.

Each of the aforementioned systems, devices, assemblies, and methods may be used to treat a target treatment site with a modular medical device capable of selective assembly and disassembly. By providing a medical device with reusable and disposable components capable of establishing mechanical, electrical, and fluidic connection with one another, instances of material waste from fully disposable devices, and cross-contamination between patients through use of fully reusable devices, may be minimized.

It will be apparent to those skilled in the art that various modifications and variations may be made in the disclosed devices and methods without departing from the scope of the disclosure. Other aspects of the disclosure will be apparent to those skilled in the art from consideration of the specification and practice of the features disclosed herein. It is intended that the specification and examples be considered as exemplary only.

We claim:

1. A medical device, comprising:
   a first body including:
      a first actuation wire having a first connector that extends outwardly from the first body; and
   a second body including:
      a second actuation wire having a second connector that is disposed within the second body, wherein the second connector includes a housing having a ball bearing that is movable within the housing between a locked position and an unlocked position;
   wherein the first connector is configured to engage the second connector in response to the second body mating with the first body, and to deform the second connector in response to the first body disengaging the second body.

2. The medical device of claim 1, wherein the first connector includes a plug having a base and a tip, and the second connector includes a barb having an opening and an internal cavity sized to receive the tip through the opening;
   wherein the base is configured to engage the barb to form a stop between the plug and the barb.

3. The medical device of claim 1, wherein the second connector includes a maximum force tolerance, and the first connector is configured to deform the second connector when the first actuation wire applies a force to the first connector that exceeds the maximum force tolerance.

4. The medical device of claim 1, wherein the second actuation wire moves relative to the second body in response to the first actuation wire moving relative to the first body.

5. The medical device of claim 1, wherein the second connector is fixed to a port of the second body; and
   wherein the first actuation wire is configured to remove the second connector from the port in response to the first connector engaging the second connector and moving relative to the first body.

6. The medical device of claim 5, wherein the second connector is configured to expand when removed from the port, such that the second connector is inhibited from reentering the port.

7. The medical device of claim 1, wherein the first body includes a first fluidics port, and the second body includes a second fluidics port that mates with the first fluidics port when the second body mates with the first body.

8. The medical device of claim 7, wherein a seal is formed between the first fluidics port and the second fluidics port when the second body mates with the first body at a plurality of axial positions.

9. The medical device of claim 1, wherein the second body includes a latch that is configured to engage the first body to fix an axial position of the first body relative to the second body.

10. The medical device of claim 1, wherein the first connector is configured to move the ball bearing within the housing when the second body mates with the first body.

11. The medical device of claim 1, wherein the ball bearing is configured to allow movement of the first connector through the housing when in the unlocked position, and inhibit movement of the first connector through the housing when in the locked position.

12. The medical device of claim 11, wherein the housing defines a cavity having a narrowed portion and a widened portion that is wider than the narrowed portion; and
   wherein the ball bearing is positioned within the cavity adjacent to the wider portion when in the unlocked position, and adjacent to the narrowed portion when in the locked position.

13. The medical device of claim 1, wherein the first body includes a distal end having a first asymmetric profile, and the second body includes a proximal end having a second asymmetric profile corresponding to the first asymmetric profile.

14. The medical device of claim 13, wherein the second body is configured to mate with the first body in a first orientation when the first asymmetric profile is aligned with the second asymmetric profile, and inhibit mating with the first body in a second orientation when the first asymmetric profile is misaligned with the second asymmetric profile.

15. A medical device, comprising:
   a handle including:
      a first body;
      a first actuation wire; and
      a first connector coupled to the first actuation wire, wherein the first connector is movable relative to the first body in response to movement of the first actuation wire; and
   a distal portion including:
      a second body;
      a second actuation wire; and
      a second connector coupled to the second actuation wire, wherein the second connector includes a housing having a ball bearing that is movable within the housing between a locked position and an unlocked position, wherein the second connector is movable relative to the second body in response to movement of the second actuation wire;
   wherein the handle is configured to move the first actuation wire and the second actuation wire when the handle is mated with the distal portion and the first connector is engaged with the second connector; and
   wherein the second connector is configured to deform when the handle is disengaged from the distal portion.

16. The medical device of claim 15, wherein the handle is configured to move the first connector and the second connector relative to the second body when the handle is mated with the distal portion and the first connector is engaged with the second connector.

17. The medical device of claim 16, wherein the distal portion includes a movable latch that engages the handle to secure the first body to the second body; and
    wherein the movable latch is at least partially deformed in response to engaging the first body.

18. The medical device of claim 15, further comprising a ring movably coupled to the distal portion, and configured to engage the handle when the handle is mated with the distal portion;
    wherein the ring is configured to couple the first connector with the second connector, and apply tension to the first actuation wire and the second actuation wire.

19. A medical device, comprising:
    a first body including:
        a first actuation wire;
        a first connector coupled to the first actuation wire and extending distally from the first body; and
        a fluid channel;
    a second body including:
        a second actuation wire;
        a second connector coupled to the second actuation wire, wherein the second connector includes a housing having a ball bearing that is movable within the housing between a locked position and an unlocked position; and
        a fluid tube extending proximally from the second body;
    wherein the first connector is configured to engage the second connector, and the fluid channel is configured to mate with the fluid tube, in response to the second body mating with the first body; and
    wherein the first connector is configured to alter the second connector so that the second connector cannot engage the first connector, and the fluid channel is configured to disengage with the fluid tube, in response to the first body disengaging from the second body.

\* \* \* \* \*